(12) United States Patent
Gierhart et al.

(10) Patent No.: US 12,106,861 B2
(45) Date of Patent: *Oct. 1, 2024

(54) DIAGNOSTIC, PRESCRIPTIVE, AND DATA-GATHERING SYSTEM AND METHOD FOR MACULAR PIGMENT DEFICITS AND OTHER EYE DISORDERS

(71) Applicant: ZeaVision LLC, Chesterfield, MO (US)

(72) Inventors: Dennis L. Gierhart, Chesterfield, MO (US); Terry B. Hatfield, St. Louis, MO (US)

(73) Assignee: ZeaVision LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/173,070

(22) Filed: Feb. 23, 2023

(65) Prior Publication Data
US 2023/0197292 A1 Jun. 22, 2023

Related U.S. Application Data

(63) Continuation of application No. 16/780,773, filed on Feb. 3, 2020, now Pat. No. 11,594,336, which is a
(Continued)

(51) Int. Cl.
*G16H 70/20* (2018.01)
*A61B 3/00* (2006.01)
(Continued)

(52) U.S. Cl.
CPC ........... *G16H 70/20* (2018.01); *A61B 3/0025* (2013.01); *A61B 3/10* (2013.01); *A61B 3/12* (2013.01);
(Continued)

(58) Field of Classification Search
CPC ........ G16H 70/20; G16H 10/60; G16H 15/00; G16H 20/10; G16H 20/60; G16H 40/20;
(Continued)

(56) References Cited

U.S. PATENT DOCUMENTS

| 5,747,544 A | 5/1998 | Garnett |
| 5,827,652 A | 10/1998 | Garnett |

(Continued)

OTHER PUBLICATIONS

International Search Report for PCT/US07/01798, dated Dec. 5, 2007, 3 pages.
(Continued)

*Primary Examiner* — Mohammed A Hasan
(74) *Attorney, Agent, or Firm* — Nixon Peabody LLP

(57) ABSTRACT

A macular health measurement and storage system comprises a plurality of macular-pigment measurement machine for measuring macular pigment density in humans, a plurality of computers each of which is associated with a corresponding one the macular-pigment measuring machines, and a central host. The plurality of macular-pigment measurement machines include a device for receiving macular pigment data from a patient, at least one data transfer port, and at least one processor that enables the transfer of the macular pigment data from the transfer port. The plurality of computers include a first port coupled to the data transfer port of the corresponding macular-pigment measurement machine for receiving the macular pigment data. Each of the computers includes a second port for transferring patient data. The central host is coupled to the second ports on each of the plurality of computers. The central host includes a storage device for storing the patient data.

26 Claims, 7 Drawing Sheets

Related U.S. Application Data continuation of application No. 16/006,650, filed on Jun. 12, 2018, now Pat. No. 10,548,471, which is a continuation of application No. 15/256,237, filed on Sep. 2, 2016, now Pat. No. 10,016,126, which is a continuation of application No. 14/792,315, filed on Jul. 6, 2015, now Pat. No. 9,445,715, which is a continuation of application No. 14/102,346, filed on Dec. 10, 2013, now Pat. No. 9,095,279, which is a continuation of application No. 13/794,791, filed on Mar. 12, 2013, now Pat. No. 8,632,179, which is a continuation of application No. 13/087,005, filed on Apr. 14, 2011, now Pat. No. 8,408,702, which is a continuation of application No. 12/294,827, filed as application No. PCT/US2007/001798 on Jan. 22, 2007, now Pat. No. 7,942,526.

(60) Provisional application No. 60/761,712, filed on Jan. 23, 2006.

(51) Int. Cl.
*A61B 3/10* (2006.01)
*A61B 3/12* (2006.01)
*A61B 3/14* (2006.01)
*A61B 5/00* (2006.01)
*G16H 10/60* (2018.01)
*G16H 15/00* (2018.01)
*G16H 20/10* (2018.01)
*G16H 20/60* (2018.01)
*G16H 40/20* (2018.01)
*G16H 40/67* (2018.01)
*G16H 50/20* (2018.01)
*G16Z 99/00* (2019.01)

(52) U.S. Cl.
CPC .............. *A61B 3/14* (2013.01); *A61B 5/7275* (2013.01); *G16H 10/60* (2018.01); *G16H 15/00* (2018.01); *G16H 20/10* (2018.01); *G16H 20/60* (2018.01); *G16H 40/20* (2018.01); *G16H 40/67* (2018.01); *G16H 50/20* (2018.01); *G16Z 99/00* (2019.02)

(58) Field of Classification Search
CPC ........ G16H 40/67; G16H 50/20; G16H 50/70; A61B 3/0025; A61B 3/10; A61B 3/12; A61B 3/14; A61B 5/7275; G16Z 99/00
USPC ........................................................ 351/205
See application file for complete search history.

(56) References Cited

U.S. PATENT DOCUMENTS

| | | | |
|---|---|---|---|
| 5,854,015 | A | 12/1998 | Garnett |
| 6,017,122 | A | 1/2000 | Bone |
| 6,236,877 | B1 | 5/2001 | Elsner |
| 6,315,412 | B1 | 11/2001 | Snodderly |
| RE38,009 | E | 2/2003 | Garnett |
| 6,936,279 | B2 | 8/2005 | Guerra-Santos |
| 7,331,669 | B2 | 2/2008 | Elsner |
| 7,441,896 | B2 | 10/2008 | Bone |
| 7,467,870 | B2 | 12/2008 | van de Kraats |
| 8,408,702 | B2 | 4/2013 | Gierhart |
| 8,632,179 | B2 | 1/2014 | Gierhart |
| 9,095,279 | B2 | 8/2015 | Gierhart |
| 9,433,346 | B2 | 9/2016 | Huang |
| 9,445,715 | B2 | 9/2016 | Gierhart |
| 10,016,126 | B2 | 7/2018 | Gierhart |
| 10,548,471 | B2 | 2/2020 | Gierhart |
| 11,594,336 | B2* | 2/2023 | Gierhart .................. A61B 3/14 |
| 2002/0101566 | A1 | 8/2002 | Elsner |
| 2003/0108598 | A1 | 6/2003 | Garnett |
| 2004/0081628 | A1 | 4/2004 | Gierhart |
| 2004/0207811 | A1 | 10/2004 | Elsner |
| 2005/0010115 | A1 | 1/2005 | Bone |
| 2005/0147648 | A1 | 7/2005 | Gierhart |
| 2005/0171212 | A1 | 8/2005 | Gierhart |
| 2006/0039954 | A1 | 2/2006 | Gierhart |
| 2006/0089411 | A1 | 4/2006 | Gierhart |
| 2006/0134004 | A1* | 6/2006 | Gellermann ......... A61B 5/0059 600/315 |
| 2007/0082066 | A1 | 4/2007 | Gierhart |
| 2007/0252950 | A1* | 11/2007 | Kraats .................... A61B 3/156 351/221 |
| 2007/0270673 | A1 | 11/2007 | Abrams |
| 2010/0241450 | A1* | 9/2010 | Gierhart .................. A61B 3/12 351/205 |
| 2012/0008093 | A1* | 1/2012 | Spaide .................... A61B 3/14 351/206 |
| 2012/0092619 | A1* | 4/2012 | Rowe .................. A61B 3/0016 351/221 |

OTHER PUBLICATIONS

Van Norren, Dirk,, "Fast and objective measurement of macular Pigment with Natural Pupil", Department of Ophthalmology, UMC Utrecht, University Eye Clinic Maastricht (2005).

Bour, Lo J.,, Fundus Photography for Measurement of macular Pigment Density Distribution in Children, Investigative Ophthalmology & Visual Science, May 2002, vol. 43, No. 5, pp. 1450-1456.

Robson, Anthony G.,, "Comparison of Fundus Autoflourescence and Minimum-motion Measurements of Macular Pigment Distribution Profiles Derived from Identical Retinal Areas", Perception, Jun. 2005, vol. 34, pp. 1027-1032.

Moreland, JD., "Macular Pigment Assessment by Motion Photometry", NCBI.gov., National Library of Medicine, MacKay Institute, Keele University, Oct. 2004, 1 page.

Snodderly, D. Max, "Macular Pigment Measurement by Heterochromatic Flicker Photometry in Older Subjects: The Carotenoids and Age-Related eye Disease Study", Investigative Ophthalmology & Visual Science, Feb. 2004, vol. 45, No. 2, pp. 531-538.

Wooten, Billy R., "A Practical Method for Measuring Macular Pigment Optical Density", Investigative Ophthalmology & Visual Science, Oct. 1999. vol. 40, No. 11, pp. 2481-2489.

Eyemet Macular Pigment, University of Westminster, Vision Research Group, 10 pages, Aug. 2011.

Bone, RA, "Heterochromatic Flicker Photometry", NCBI.gov., National Library of Medicine, Department of Physics, Florida University, Arch Biochem Biophys, Oct. 2004, 1 page.

Mellerio, J.,, "A Portable Instrument for Measuring Macular Pigment with Central Fixation", NCBI.gov, National Library of Medicine, School of Biosciences, University of Westminster, London, UK, Curr Eye Res., Jul. 2002, 1 page.

Delori FC,, "Macular Pigment Density Measured by Autoflourescence Spectrometry: Comparison with Reflectometry and Heterochromatic Flicker Photometry", NCBI.gov, National Library of Medicine, Schepens Eye Research Institute, Boston, MA, J Opt Soc Am A Opt Sci Vis., Jun. 2001, 1 page.

Delori, Francois C., "Autofluorescence Method and Measure Macular Pigment Optical Densities Fluorometry and Autofluorescence Imaging", Schepens Eye Research Institute and Harvard Medical School, Boston, MA, Mar. 2004, pp. 1-7.

Bernstein, Paul S., "Resonance Raman Measurement of Macular Carotenoids in the Living Human Eye", Department of Ophthalmology and Visual Sciences, Moran Eye Center, University of Utah School of medicine, Salt Lake City, UT, Mar. 2004, pp. 1-7.

Berendschot,, "Influence of Lutein Supplementation on Macular Pigment, Assessed with Two Objective Techniques", Investigative Ophthalmology and Visual Science, The Association for Research in Vision and Ophthalmology, Inc., Mar. 2000, 1 page.

Berendschot,, "Objective Determination of the Macular Pigment Optical Density Using Fundus Reflectance Spectroscopy", Department of Ophthalmology, University Medical Center Utrecth, the Netherlands, Mar. 2004, pp. 149-155.

(56) References Cited

OTHER PUBLICATIONS

Zarbin, Marco A., "Current Concepts in the Pathogenesis of Age-Related Macular Degeneration", Mechanisms of Ophthalmic Disease, Apr. 2004 American Medical Association, pp. 598-614.

Hammond BR. Jr., "Assessment of the Validity of in Vivo Methods of Measuring Human Macular Pigment Optical Density", NCBI.gov, National Library of Medicine, Vision Science Laboratory, University of Georgia, Athens, Georgia, Optom Vis Sci., May 2005, 1 page.

Celentano, Joanne Curran, "In Vivo Assessment of Retinal Carotenoids: Macular Pigment Detection Techniques and Their Impact on Monitoring Pigment Status", Symposium: Can Lutein Protect Against Chronic Disease?, American Society for Nutritional Sciences, Department of Animal and Nutritional Sciences, University of New Hampshire, Durham, NH, May 2002, pp. 535S-539S.

D'Amato, Robert M.D. Phd., "Macular Degeneration, the Latest Scientific Discoveries and Treatments for Preserving Your Sight", Walker Publishing Co., Inc., May 2000, 2 pages.

Sangiovanni, JP., "A New PC-based Method of Measuring Visual Acuity in Clinical Trials", The Association for Research in Vision and Ophthalmology, Presentation No. 874, 2000, 2 pages.

Dagnelie, G., Validated Vision Test Battery for the Home PC, Investigative Ophthalmology & Visual Science. The Association for Research in Vision and Ophthalmology, Presentation No. 3811, 2002, 2 pages.

Eshraghi, Fariba,, Abstract #57, "Validation of PC-Based Visual Function Measures for Use in Clinical Trials", 11 pages, Mar. 2000.

Dagnelie, G.,, "Lutein Improves Visual Function in Some Patients with Retinal Degeneration: a Pilot Study via the Internet", NCBI.gov, National Library of Medicine, Johns Hopkins University School of medicine, Baltimore, MD, Mar. 2000, 1 page.

Packer, Lester Phd, "How do you Know Your Supplements are Working", Biophotonic Scanner, Pharmanex Brochure, Mar. 2003, 7 pages.

Lim, Jennifer, "Age-Related Macular Degeneration", Marcel Dekker, Inc. Brochure, 3 pages, Jul. 2002.

Gellerman, W. "Noninvasive Detection of Macular Pigments in the Human Eye." Journal of Biomedical Optics., vol. 9, No. 1, Jan. 2004, pp. 75-85 (11 pages).

\* cited by examiner

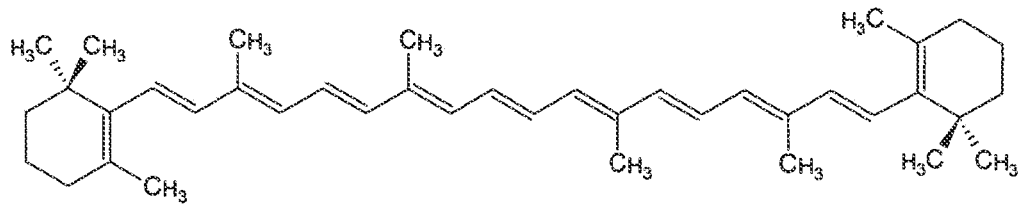
Beta-carotene -- no oxygen atoms, not a "xanthin" carotenoid
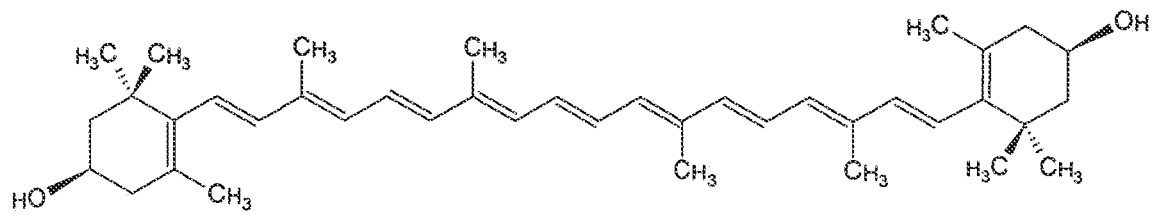
3R,3'R-zeaxanthin -- entirely symmetric, beta rings at both ends
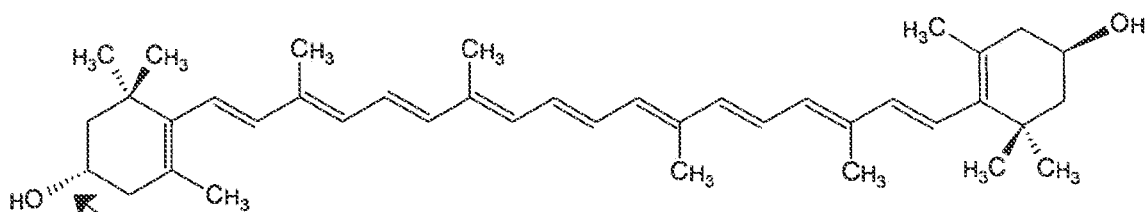
S,R ("meso") zeaxanthin -- not symmetric, hydroxy group at one end points down, never found in diet or blood
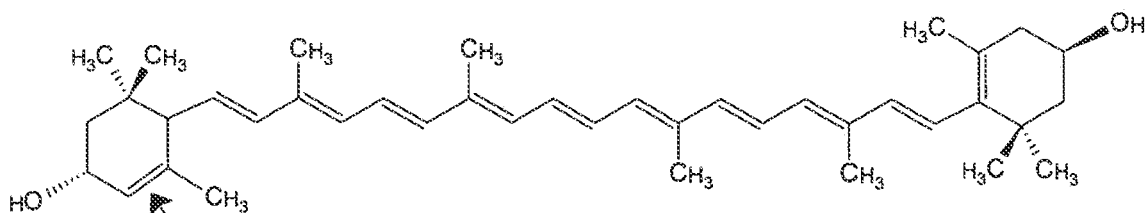
Lutein -- "epsilon" end ring has non-conjugated sequence, no electron cloud to absorb UV or radicals
*Fig. 1*

WELCOME STEVE GIERFIELD-ENTER INFO

1. EYE COLOR — BLUE
2. AGE — 58
3. GENDER — MALE
4. SMOKER — NO
5. DIAGNOSED AMD — NO
6. HIGH BLOOD PRESSURE — YES
7. DAILY VITAMIN — NO
8. CATARACTS, GLAUCOMA — NO
9. FIVE DAILY SERVINGS OF VEGGIES / FRUIT — YES
10. DAILY EYE VITAMIN — NO
11. BODY MASS INDEX — 25 kg/m²

WELCOME STEVE GIERFIELD-YOUR TEST IS COMPLETE!!

YOUR MPOD TEST RESULT IS - 0.22

MPOD ABOVE 0.40 - GOOD

MPOD 0.30-0.40 - AVERAGE

MPOD 0.20-0.30 - BELOW AVERAGE

MPOD LESS THAN 0.20 - LOW

YOUR RESULTS WILL BE SAVED AND DR. BENSON WILL CONSULT WITH YOU 11-05-04

*Fig. 5*

WELCOME BACK STEVE GIERFIELD-CONFIRM INFO

1. EYE COLOR — BLUE
2. AGE — 58
3. GENDER — MALE
4. SMOKER — NO
5. DIAGNOSED AMD — NO
6. HIGH BLOOD PRESSURE — YES
7. DAILY VITAMIN — NO
8. CATARACTS, GLAUCOMA — NO
9. DAILY SERVINGS OF VEGIES / FRUIT — YES
10. DAILY EYE VITAMIN — YES
11. BODY MASS INDEX — 25 kg/m²

WELCOME STEVE GIERFIELD-YOUR TEST IS COMPLETE!!

YOUR MPOD TEST RESULT IS - 0.31

MPOD ABOVE 0.40 - GOOD

MPOD 0.30-0.40 - AVERAGE

MPOD 0.20-0.30 - BELOW AVERAGE

MPOD LESS THAN 0.20 - LOW

YOUR RESULTS WILL BE SAVED AND DR. BENSON WILL CONSULT WITH YOU

DIAGNOSTIC, PRESCRIPTIVE, AND DATA-GATHERING SYSTEM AND METHOD FOR MACULAR PIGMENT DEFICITS AND OTHER EYE DISORDERS

CROSS REFERENCE TO RELATED APPLICATIONS

This application is a continuation of U.S. application Ser. No. 16/780,773, filed Feb. 3, 2020, now allowed, which is a continuation of U.S. application Ser. No. 16/006,650, filed Jun. 12, 2018, now issued as U.S. Pat. No. 10,548,471, which is a continuation of U.S. application Ser. No. 15/256,237, filed Sep. 2, 2016, now issued as U.S. Pat. No. 10,016,126, which is a continuation of U.S. application Ser. No. 14/792,315, filed Jul. 6, 2015, now issued as U.S. Pat. No. 9,445,715, which is a continuation of U.S. application Ser. No. 14/102,346, filed Dec. 10, 2013, now issued as U.S. Pat. No. 9,095,279, which is a continuation of U.S. application Ser. No. 13/794,791, filed Mar. 12, 2013, now issued as U.S. Pat. No. 8,632,179, which is a continuation of U.S. application Ser. No. 13/087,005, filed Apr. 14, 2011, now issued as U.S. Pat. No. 8,408,702, which is a continuation of U.S. application Ser. No. 12/294,827, filed Sep. 26, 2008, now issued as U.S. Pat. No. 7,942,526, which is a U.S. national phase of International Application No. PCT/US2007/001798, filed Jan. 22, 2007, which claims the benefit of priority of U.S. Provisional Patent Application No. 60/761,712, filed Jan. 23, 2006, each of which is incorporated by reference in its entirety.

FIELD OF THE INVENTION

This invention is in the fields of eye care, nutritional supplements, and diagnostic methods and systems, and relates to both: (i) a computerized device that can be installed and used in a single location (e.g. a optometrist's office) for diagnosing abnormal macular pigment levels, which may eventually cause vision loss; and, (ii) a distributed computer system that links computers at many locations to a centralized computer that compiles and analyzes data to create improved risk assessments and better prevention and intervention treatments.

BACKGROUND OF THE INVENTION

Nutritional supplements, which play important roles in preserving eye health, can be purchased "over-the-counter" (i.e., without requiring a prescription from a physician) and are usually taken in unit dosages. Nutritional supplements, which contain nutrients that occur naturally in a healthy diet, are very different from prescription drugs, which (in the United States) can be sold only by pharmacies that require a prescription from a doctor. "Nutrients" are compounds that are often found in a normal human diet and/or a healthy human body (this can include precursors, etc.), regardless of whether they are synthesized chemically, or extracted from natural sources. The term "nutrients" is generally intended to be distinct from pharmaceuticals, antibiotics, and other "xenobiotic" compounds that are not normally found in natural sources. "Unit dosage" forms comprise formulations designed to enable a user to know and control the quantity of a nutrient or nutritional supplement that is being ingested each day. Unit dosage formulations include, for example, tablets and capsules (which includes hybrid-type pills, such as coated tablets, "caplets", etc.), powders or liquids that are accompanied by measuring and quantity instructions. However, the present invention can be useful if levels of a supplement exceed predetermined levels such that the nutritional supplement is a "prescribed" nutritional supplement.

One problem associated with nutritional supplements relates to whether they assist each individual in preventing eye disorders or helping to treat eye disorders. Another problem is that some individuals have the perception that their diet is "acceptable," when, in fact, it is deficient in providing certain nutrients. As such, many individuals who may benefit from nutritional supplements are often reluctant to use nutritional supplements. As such, what is needed is a system and method that allows individuals to easily understand the beneficial effects that will occur if the patient takes the nutritional supplement for a short period of time, such as several weeks or several months (e.g., every 6 months).

Nutritional supplements can provide (i) health-sustaining benefits, when used as preventive (or prophylactic) agents by someone who is relatively healthy, and/or (ii) disease-treating benefits, when used as therapeutic (or treatment) agents by someone who is suffering from a known disorder (therapeutic use is often referred to also as drug use). The distinction between preventive use versus therapeutic use depends on the status of the person being treated, and that status often falls into an unknown, "early onset", or other borderline or boundary area where the proper category is not always clear. It should also be recognized that preventive (prophylactic) use normally involves lower dosages, while therapeutic use usually involves higher dosages.

As discussed below, this invention relates to a computerized system that enables front-line eye-specialists to become actively involved in a nationwide and worldwide data-gathering system, that focuses upon (but is not limited to) measuring and analyzing macular pigment, which is important to preventing and treating a number of eye and vision diseases, including macular degeneration. As used herein, a "front-line eye specialist" includes any person (e.g., a health care worker) who is trained and qualified to work with individuals to allow measurements to be taken of the patient's eyes via the devices listed below. The definition includes optometrists and other eye vision centers, that are often the first and, in many cases, the only eye care specialists that most people will ever see. Front-line eye specialists also include health-care workers who work in hospitals and nursing homes in which patients are treated. Ophthalmologists, who are highly-trained eye specialists, can also serve to provide "front line" eye care, and may be included as well.

As such, the role of front-line eye specialist in actually preventing eye diseases and blindness will become substantially greater because they will be in the ideal position to take the necessary "first steps" toward ensuring that their clients, customers, and patients begin receiving and taking suitable nutritional supplements to help those clients, customers, and patients preserve their eyes and vision, as soon as possible, to minimize the extent of early and potentially irreversible loss and damage.

With the foregoing as preface, the remainder of the description below focuses on a group of retinal diseases that are collectively referred to as "retinal degeneration" and the use of nutritional supplements (in particular, zeaxanthin and lutein) that will help prevent and treat patients with the retinal degeneration. Retinal degeneration includes macular degeneration and diabetic retinopathy.

The Retina, the Macula, and Macular Degeneration: The retina is the layer of nerve cells at the back of the eye, which convert light into nerve signals that are sent to the brain. In humans, and in other primates (but not in most other mammals, or other types of animals), the retina has a small yellowish area in the center of the field of vision. That yellowish area is called the "macula." It provides fine-resolution vision in the center of the visual field, and it is essential to good vision. People who suffer from macular degeneration often lose the ability to read, recognize faces, drive, or walk safely on unfamiliar routes.

The surrounding portions of the retina can only provide coarse resolution. This physiological feature limits and controls the number of nerve signals that the brain must rapidly process, to form coherent rapid-response vision, and it also helps limit and control the huge number of rod and cone receptors that the eye must continually regenerate and recycle, every day. Many people do not realize the retina can provide only coarse resolution, outside of a limited central area, because the eyes and the brain have developed an extraordinary ability to synthesize coherent vision from a combination of fine and coarse resolution. During that type of vision synthesis, the eye muscles cause the eyes to flit back and forth over a larger field of vision, pausing at each location for just an instant while the eye quickly "grabs" a fine-resolution image of a limited area. This process occurs so rapidly that a person doesn't notice it happening, and doesn't pay attention to how a complete visual image and impression is being assembled and updated from combinations of fine and coarse resolution images.

However, the steps and components that are involved in how vision is created, not just by the eyes but by the brain as well, can be recognized, if someone pays particular attention to various aspects of it. As a simple demonstration, if someone focuses intently on a single word, on a printed page, it is effectively impossible for that person to read any words that are only an inch above or below the word that is being focused upon, at the center of the field of vision. Similarly, someone who begins to suffer from "macular degeneration" will be forced to realize how important fine resolution is, in human vision. That type of fine resolution is provided only by the macula, and the macula covers only the center portion of the field of vision.

There is also a peculiar anatomic structure in the retinas of humans, which points out the difference between fine resolution (provided by the macula) and coarse resolution (provided by the remainder of the retina). In humans, the blood vessels that serve the retina actually sit in front of the retina, where they can block and interfere with incoming light, before the light reaches the retina. This is counter-intuitive, and one should wonder why the retina evolved with a physical handicap that literally gets in the way of good, clear vision. The answer is, in those parts of the retina, only coarse vision is being created, and blood vessels positioned in front of the retina do not interfere with that type of coarse vision. By contrast, in the macular region in the center of the retina, the blood vessels are moved back, and positioned behind the layer of neurons with rod and cone receptors. This is consistent with the macula providing fine resolution vision, which would be blocked and hindered if the blood vessels were located in front of the neurons, in ways that would intercept and blocking portions of the incoming light.

"Retinal degeneration" is a descriptive term, which refers to and includes an entire class of eye diseases and disorders. It includes any progressive disorder or disease that causes the macula to gradually degenerate, to a point that substantially impairs or damages eyesight and vision. Several major categories of retinal degeneration are known. These include: (i) age-related macular degeneration, which gradually appears among some people over the age of about 65; (ii) diabetic retinopathy, in which problems with sugar and energy metabolism damage the entire retina, including the macula; (iii) eye diseases that affect the macula due to gene and/or enzyme defects, such as Stargardt's disease, Best's disease, Batten's disease, Sjogren-Larsson syndrome, and various other eye disorders that lead to gradual degeneration of the macula (and possibly other parts of the retina) over a span of time. That is not an exclusive list, and other subclasses and categories also are known. For example, age-related macular degeneration is subdivided into wet and dry forms, depending on whether abnormal and disruptive blood vessel growth is occurring in the structural layers behind the retina.

The causes and effects of macular degeneration, and efforts to prevent or treat it, are described in numerous books (e.g., "Macular Degeneration," by Robert D'Amato et al (2000) and "Age-Related Macular Degeneration," by Jennifer Lim (2002)), articles ("Age-Related Macular Degeneration" by Berger et al (1999)) and patents, such as U.S. Pat. No. Re. 38,009, which is assigned to ZeaVision LLC, and is incorporated by reference in its entirety.

In recent years, awareness has grown, among some researchers but not among the general public, of the roles that macular pigment plays, in the health and longevity of the macula. Therefore, the two carotenoid pigments that create and provide the macular pigment are discussed below.

The Macular Pigments: Zeaxanthin and Lutein: The macula has a yellowish color because it contains unusually high concentrations of two specific pigments, called zeaxanthin and lutein. Both are carotenoids, similar to beta-carotene but with hydroxy groups coupled to their end rings (the presence of one or more oxygen atoms causes a carotenoid to be categorized as a "xanthophyll", so zeaxanthin and lutein are sometimes referred to as xanthophylls). Both of those two carotenoids are known to be protective and beneficial, in human retinas, by mechanisms that include: (1) absorption of destructive ultraviolet photons; and (2) quenching of destructive radicals. Both of those mechanisms, and other potential protective mechanisms, are discussed below.

In addition to their involvement in the macula and macular degeneration, zeaxanthin and lutein also are present in other eye structures (including lenses), and undesirably low levels of those two carotenoids appear to be correlated with higher risks of disorders such as cataracts. Accordingly, although the discussion herein focuses on macular degeneration, it should be recognized that any comments herein about macular pigment levels also have varying degrees of relevance to some other eye disorders as well. Similarly, any comments herein about macular degeneration should be recognized as including disorders that are referred to by other names (such as diabetic retinopathy, Stargardt's disease, etc.), but that involve or lead to gradual deterioration of the macula.

The structures of zeaxanthin and lutein are shown in FIG. 1. They are very similar, and are isomers of each other, differing only in the placement of a double bond in one end ring, as indicated by the arrow in FIG. 1. In lutein, the ring with a "misplaced" double bond is called an "epsilon" ring. All of the other end rings shown in FIG. 1 have "beta" ring structures, which refers to the sequence of double bonds found in beta-carotene's two end rings.

However, that single minor structural difference, between zeaxanthin versus lutein, has profound effects on the traits, performance, and tissue concentrations of those two different molecules, in both plants and animals. Briefly, the lutein molecule has a bend where the epsilon ring joins the "straight chain" segment between the two end rings. That bend, near one end, allows lutein to fit properly into ring-shaped "light-harvesting" structures, in the chloroplasts of plant cells. Since light-harvesting (which is part of photosynthesis) is crucial in plants, lutein evolved as a major and dominant carotenoid, in essentially all plants.

By contrast, zeaxanthin does not have a bend at either end. Since it is relatively straight, it cannot fit properly into the circular light-harvesting structures that help carry out photosynthesis, in plants. Therefore, it evolved in plants in ways that led to a very different role in a day-night cycle, in which zeaxanthin and a similar carotenoid called violaxanthin are converted back and forth into each other. As a result, zeaxanthin does not accumulate in substantial quantities in most types of plants (although a few exceptions are known, such as corn and red peppers). Even in dark green plants, such as spinach or kale, lutein content is dozens or even hundreds of times greater than zeaxanthin content. On an aggregate basis, the total amount of zeaxanthin in typical diets in industrial nations is believed to be about 1% (or possibly even less) of the total lutein supply.

Another major difference between them is that lutein can be obtained in bulk, and at low cost, from the orange flowers of marigolds. Since that source is available and inexpensive, lutein from marigolds has been used for decades as a major coloring pigment, in poultry and farm-raised salmon. In poultry, lutein causes the skin and yolks to turn yellow, which becomes a deeper golden tint when a red pigment is also added. That golden tint is appealing to consumers; without it, chicken meat that is packaged and refrigerated for sale in a store tends to have a pale, bleached, pasty appearance, and does not look fresh or appealing. In contrast, no comparable supplies of zeaxanthin in bulk have been available, and the development and use of zeaxanthin lagged far behind lutein. It should be noted that the majority of currently available supplies of lutein contain relatively small quantities of zeaxanthin (e.g. about 5% or less). In fact, for a number of years, zeaxanthin was regarded by some lutein sellers in their sales materials, as merely an impurity in their lutein. The first large-scale commercial sales of concentrated zeaxanthin, for ingestion by humans, did not begin until 2002, when Roche Vitamins (subsequently purchased by DSM Chemicals) began selling a synthetic version, which was encapsulated and sold by various retailers, including ZeaVision LLC, the assignee herein. Ingestion of zeaxanthin by a human provides benefits to the macula.

Another important difference between zeaxanthin and lutein is that zeaxanthin has a longer and more protective "conjugated cloud" of electrons surrounding it, compared to lutein. When a series of carbon atoms are bonded to each other by alternating double and single bonds, the electrons become mobile, and are no longer affixed to specific bond locations. Those electrons form a flexible and movable electron "cloud". This same type of cloud also appears in benzene rings and other "aromatic" organic compounds, and it is well-known to chemists.

That type of flexible and movable electron cloud is ideally suited for absorbing high-energy radiation (in the ultraviolet, near-ultraviolet, and deep blue part of the spectrum), without suffering damage or breakage of the molecule. In addition, a flexible and movable electron cloud is ideally suited for neutralizing and "quenching" oxygen radicals, which are aggressively unstable and destructive molecules, containing oxygen atoms having unpaired electrons. Oxidative radicals are important damaging agents in any cells and tissues that are being bombarded by high levels of UV radiation, since UV radiation often breaks bonds that involve oxygen atoms, in ways that create unpaired electrons where the broken bonds previously existed.

All carotenoids are assembled, in plants, from a 5-carbon precursor called isoprene, which has two double bonds separated by a single bond. As a result, all carotenoids have at least some sequence of alternating double and single bonds, leading to a conjugated electron cloud covering at least part of the carotenoid molecule. This is a basic and shared trait of all carotenoids, and it explains how carotenoids provide two crucial benefits (i.e., absorption of UV radiation, and quenching of destructive radicals) that are vital to plants, which must often sit in direct sunlight for hours each day.

However, different carotenoids have conjugated electron clouds that different lengths, and different potencies and protective traits. In particular, there is a crucial difference between the conjugated electron clouds of zeaxanthin, and lutein. As shown in FIG. 1, the placement of the double bonds in both of zeaxanthin's two end rings continues and extends the pattern of alternating double and single bonds, from the straight chain. This extends zeaxanthin's conjugated and protective electron cloud, out over a part of both of zeaxanthin's two end rings.

By contrast, as shown in FIG. 1, the position of the double bond in lutein's "epsilon" ring disrupts the alternating double/single bond sequence, established by the straight-chain portion of the molecule. This disrupts and terminates the conjugated electron cloud, and it prevents the protective, UV-absorbing, radical-quenching electron cloud from covering any part of lutein's epsilon end ring.

That structural difference in their end rings becomes highly important, because zeaxanthin and lutein are deposited into animal cells in ways that cause them to "span" or "straddle" the outer membranes of the cells. It causes zeaxanthin and lutein to be deposited into animal cell membranes in a way that places them perpendicular to the surfaces of the membrane that surrounds and encloses a cell.

That "spanning" or "straddling" orientation, across the thickness of the outer membrane of an animal cell, arises from the presence of the two "hydrophilic" (water-seeking) hydroxy groups on the end rings of those two carotenoids. On the other hand, Beta-carotene has no hydroxy groups on either end ring. Therefore, Beta-carotene settles into the oily interior layer of a cell membrane, effectively hidden from the watery liquids that are both inside and outside of the cell. Beta-carotene eventually is broken in half, by enzymes, to release two molecules of retinol, which is Vitamin A. Nearly all carotenoids that are important in animal health and physiology are derived from beta-carotene. It is not just a coincidence that those carotenoids happen to have molecular lengths that allow them to extend a portion of both end rings, slightly beyond the surface of an animal cell membrane.

The "membrane-spanning" orientation of zeaxanthin or lutein, in animal cells, causes portions of the end rings of both molecules to be exposed on the inner and outer surfaces of an animal cell membrane. One end ring will be exposed to blood, lymph, and other "extracellular" fluids outside of the cell. The other end ring will be exposed to the watery liquid inside the cell (often called the cytoplasm or cytosol).

The "membrane-spanning" positioning of zeaxanthin, in an animal cell membrane, allows it to provide a protective electron cloud that extends outward from both the inner and outer surfaces of an animal cell membrane. On that subject, it should also be noted that zeaxanthin is completely symmetric, end-to-end. Therefore, it makes no difference which end ring of zeaxanthin is "grabbed" by an enzyme that is preparing to insert the zeaxanthin molecule into an animal cell membrane.

By contrast, since lutein has no protective electron cloud over one of its two end rings, it cannot provide a protective electron cloud extending from one of the two sides of an animal cell membrane. Furthermore, lutein is not symmetric, end-to-end, since its two end rings are different.

It is not fully known, at a molecular level, how lutein's lack of symmetry, and lack of a protective conjugated electron cloud over one end ring, affect its deposition in cells in the human macula. For example, it is not known whether the protective beta rings at one end of lutein are consistently or predominantly placed on the either the external or internal surfaces of cell membranes. In addition, it is not known whether lutein is consistently deposited, into human cell membranes, in a membrane-spanning orientation.

However, other aspects of zeaxanthin and lutein content and deposition in blood, and in the macular regions of human retinas, are well-known. Despite the rarity of zeaxanthin in food sources (as mentioned above, zeaxanthin content in typical diets is believed to be less than about 1% of the lutein supply), zeaxanthin concentrations in human blood average about 20% of lutein levels. This clearly indicates that the human body does something that indicates a selective preference for zeaxanthin, over lutein.

Even more revealingly, zeaxanthin is even more concentrated in the crucially important center of the human macula, which provides fine-resolution vision in humans. In the crucially important center of a healthy human macula, zeaxanthin is present at levels that average more than twice the concentrations of lutein. By contrast, lutein is present in higher levels around the less-important periphery of the macula. While the mechanisms which create that pattern of deposition are not fully understood, it recently has been reported that certain enzymes that appear to be involved will clearly bind to zeaxanthin with relatively high affinity under in vitro conditions; however, those same enzymes will not bind to lutein with any substantial affinity (Bhosale et al 2004).

Accordingly, these differences in how zeaxanthin and lutein are deposited in the macula provide strong evidence that the macula wants and needs zeaxanthin, more than lutein. The patterns of deposition, and the known structural and electron cloud differences, suggest and indicate that the macula wants and needs zeaxanthin, and it uses lutein only if and when it cannot get enough zeaxanthin.

This belief is also supported by another important finding. The macula may attempt to convert lutein into zeaxanthin. However, the conversion process cannot convert lutein into the normal stereoisomer of zeaxanthin found in plants and in the diet (the 3R,3'R stereoisomer). Instead, it converts lutein into a different stereoisomer that has never been found in any food sources or mammalian blood. That non-dietary isomer has one end ring with the conventional "R" configuration; however, the second end ring has an unnatural "S" configuration that is never found in the normal diet. That S—R isomer (and R—S isomer) is called meso-zeaxanthin, which is also shown in FIG. 1. It is included herein as a subset of zeaxanthin, and the machines and methods disclosed herein can be used, if desired to evaluate any benefits it may offer, in human use, although the preference is for the naturally occurring isomer of zeaxanthin.

Consequently, while lutein may have benefits, a growing body of knowledge and evidence indicates that zeaxanthin is the ideal carotenoid for helping prevent and treat the class of eye diseases that fall into the category of macular degeneration.

In light of the previous information concerning the macula and the macular pigments, this invention creates a computerized network and machines that accomplish one or more of the following functions:

(i) enable all practicing front-line specialists, such as optometrists, to rapidly diagnose the main etiologic factor that appears to cause most cases of macular degeneration (i.e., a vitamin deficiency involving low levels of the protective carotenoid, zeaxanthin), even at the very earliest stages of the disorder, which can be years before the noticeable symptoms of failing eyesight begin to trouble a patient;

(ii) provide front-line specialists with better, more convenient and affordable tools for measuring and diagnosing macular pigment levels in patients;

(iii) establish an improved but widespread and proper standard of care in ways that will greatly reduce the actual rates and risks of blindness caused by AMD;

(iv) rapidly provide much better, much more useful, and much less costly data for analysis;

(v) enable numerous front-line specialist to begin contributing useful data involving small numbers of patients from each practice, in a way that rapidly amounts to large numbers of patients in the aggregate, comparing various eye supplements (e.g., zeaxanthin v. lutein v. zeaxanthin-lutein mixtures) for actual efficacy in either preventing or treating macular degeneration;

(vi) creating a computerized network that has data-gathering and data-processing capability, which can continuously and rapidly compile, process, digest, and report large numbers of data concerning macular degeneration and efforts to treat or prevent macular degeneration, including data that will be generated in one or more multi-site, nationwide, and/or worldwide meta-trials involving intervention studies, including but not limited to intervention studies that include administration of zeaxanthin, lutein, or zeaxanthin-lutein mixtures (either with or without additional nutrient supplements, drug treatments, etc.) to people who are suffering from, or who are at elevated risk of, macular degeneration.

The invention also relates to a business method that utilizes a combination of computers, computer software, and computerized peripheral devices to enable better and more efficient prevention of vision loss and blindness, by means of low-cost systems in front-line specialists' offices. With relatively low training and operating requirements, these distributed computerized systems will be designed to provide two major sets of benefits. First, when dealing with specific patients, this system will enable front-line specialists to gather useful data concerning macular pigment levels, in any customer or patient, and rapidly provide, to any patient in need of such treatment, a nutritional supplement that can raise his or her macular pigment levels. Second, and without interfering with the goal of serving individual patients, this computerized business process described above will also enable the gathering and analysis of highly useful statistical data from thousands of patients by means of a "meta-trial" approach, in which each of hundreds or thousands of participating front-line specialists will contribute de-identified data from dozens of patents, rapidly leading to very large populations and reliable statistical analyses. This type of meta-trial testing using the computerized system disclosed herein can provide, for example, rapid and reliable data from human trials that will enable direct comparison of the actual contributions and benefits of zeaxanthin supplements, lutein supplements, or zeaxanthin-plus-lutein mixtures. As another example, this type of meta-trial testing using the computerized system disclosed herein can enable the testing and evaluation of multiple differing combinations of various known candidate active ocular agents, in ways that will help researchers develop a better understanding of which combinations of such agents will provide the most benefits, either for all patients, or for specific categories of patients.

Devices exist that measure a patient's macular pigment density. And, at least one attempt has been made to allow patients to test their macular pigment density and send the test information to a remote site, as described in "Validated Vision Test Battery for the Home PC" by Dagnelie et al (2002). However, the reliance on the video display of a home personal computer presents a high risk of error, especially when trying to correlate results for individuals having substantially different types of video displays. Further, there was no attempt to modulate or alter recommended nutritional supplements based on the data being collected by within a system. Hence, as described below, the present invention presents numerous substantial improvements to any such home PC-based type of system.

Large, cumbersome, and expensive multi-year government-run studies (such as the AREDS-1 trial done in the 1990's and reported over the 2001-2005 period, and the proposed AREDS-2 trial which has not even started yet, despite years of planning) take many years (perhaps a decade) to generate useful results. Even more importantly, despite having years to do their work and budgets of tens of millions of dollars for each study, they have been criticized as being not being able to organize and run enough different treatment arms to adequately determine or evaluate the best actual treatments.

The invention will become more apparent through the following summary, drawings, and description.

SUMMARY OF THE INVENTION

A computerized system comprises at least one hardware device that functions as a "computer peripheral" device. This device measures the patient's "macular pigment optical density" (MPOD). The device preferably transfers the MPOD data to a conventional desktop, laptop, or other computer, preferably via a standard port, such as a "universal serial bus" (USB) port and cable. In other embodiments, the MPOD device may include keyboards or touch-keys for input and a display for output, allowing for the removal of the computer in the system.

Various types of devices and methods for measuring MPOD are known, including "flicker photometer" systems that are relatively compact, inexpensive, and well-suited for placement and operation in any office, store, or other facility run by an optometrist. Such flicker photometer devices also can be emplaced and operated in the offices of ophthalmologists, teaching hospitals, eye care centers, etc., and in locations that also provide and operate more expensive and elaborate MPOD measuring systems. By using data from such locations, the ongoing performance of the flicker photometer devices can be evaluated, by comparing their results against data gathered by more elaborate and expensive systems.

On a periodic basis (such as once per week, month, or quarter), the computer at each participating front-line eye-specialist office can transfer a set of collated and processed data on MPOD readings (correlated with, for each patient, other aspects of eye health that the optometrist deemed to be relevant and worth noting and recording) to a host for gathering and processing the data from computers operated by numerous locations. Such data transfers can be made via websites or other suitable linkage or transfer modes, and can be made during late-night or other low-traffic hours, in an automated manner controlled by specialized software that will be operating at each end to enable each computer at an office to interact in a secure yet automated manner with the host. All such data gathering and transfer processes will be made in ways that fully comply with all relevant laws governing the privacy and use of medical records and informed consent by patients.

As part of the front-line eye-specialists' service for their patients, participating front-line eye-specialist will also gather and record information on the eye and vision health (or level of impairment) of each customer or patient. This can include, for example, information reported by clients on their medical history and status, information gathered by an optometrist during a personal examination, and information gathered by various "computer peripheral" devices that can be coupled to the optometrist's computer (such as, for example, data on light sensitivity, dark adaptation, shape discrimination, peripheral sensitivity in the visual field, etc., all of which can be gathered via computerized peripheral devices while a patient is waiting to be seen by an optometrist). Alternately or additionally, multi-functional computerized measuring devices can be created by additional components to an MPOD measuring device as described herein, and such multi-functional computerized devices can transfer all relevant data to the computer in a single transfer.

Depending on a patient's choices and preferences, such data can be compiled and correlated in any of various ways, such as by correlating all relevant information on macular pigment and eye health with: (i) a patient's full name; (ii) a patient's initials; or, (iii) an arbitrary code number (de-identified data) that is assigned to a patient by the optometrist, known only to the optometrist and transferred to the host so that the patient remains anonymous.

This distributed computer and peripheral system will enable trained eye-care professionals to determine and deliver truly effective prevention and treatment methods and regimens that can and will prevent cases of preventable blindness. It also will enable patients to participate, in a convenient and inexpensive way that can be satisfied with an occasional visit to any nearby office in a well-designed, well-controlled, large-scale system that can greatly advance the ability of eye care professionals to generate useful data from multiple patients, and to transfer that data rapidly and efficiently into a computerized system that can process and analyze the data, enabling data processing specialists to rapidly identify trends and correlations. It also can greatly advance the ability of eye care professionals to rapidly and efficiently generate useful data from large-scale multi-site intervention trials involving large patient populations, to evaluate the results and effects of various candidate treatment regimens. Such candidate treatment regimens can involve, for example:

(i) direct comparison of zeaxanthin-only supplements against lutein supplements (and against zeaxanthin-plus-lutein mixtures), for increasing macular pigment density, and for improving other aspects of overall eye health;

(ii) administration of various candidate agents in combinations that may be proven to have synergistic effects when combined in suitable dosages. Such combinations include, for example, zeaxanthin or possibly lutein supplements (which are regarded as the essential core of any regimen for increasing the benefits provided by the anti-oxidant and UV-absorbing macular pigment) with additional regimens of one or more of the following: Vitamins C and/or E, zinc, selenium, omega-3 fatty acids such as docosa-hexaenoic acid (DHA), carotenoids such as beta-carotene, lycopene, and/or beta-cryptoxanthin, lipoic acid, taurine, carnitine, mitochondrial booster or stabilizer agents such as glutathione, N-acetyl cysteine, or Coenzyme Q10, and plant-derived extracts or agents, such as bilberry extract, isoflavones or flavonoids from soybeans or other plants, resveratrol, etc.

By contrast, a distributed computer network with supporting software and peripheral devices, placed in the offices of hundreds of eye care professionals who are already serving thousands of patients, will enable the rapid gathering and processing of highly useful data that will serve numerous useful functions, including: (i) correlating macular pigment data with other aspects of eye health; (ii) enabling eye care professionals to administer and test macular-pigment enhancing formulas with numerous other candidate active agents, in ways that can rapidly generate statistically significant and useful data on additive and/or synergistic effects of numerous different combinations and regimens; and (iii) enabling the evaluation and compilation of statistical data on other types of eye and vision tests that may turn out to be useful indicators or predictors of eye or vision problems among the elderly.

As such, the invention can be considered a macular health measurement and storage system that comprises a plurality of macular-pigment measurement machine for measuring macular pigment density in humans, a plurality of computers each of which is associated with a corresponding one of the plurality of macular-pigment measuring machines, and a central host. The plurality of macular-pigment measurement machines include a device for receiving macular pigment data from a patient, at least one data transfer port, and at least one processor that enables the transfer of the macular pigment data from the transfer port. The plurality of computers include a first port coupled to the data transfer port of the corresponding macular-pigment measurement machine for receiving the macular pigment data. Each of the computers includes a second port for transferring patient data. The central host is coupled to the second ports on each of the plurality of computers. The central host includes a storage device for storing the patient data.

The invention can also be considered a method of addressing vision problems in individual human, comprising the act of obtaining information from patients at multiple locations, wherein the information includes macular pigment data obtained via macular-pigment measurement machines at the locations. The macular-pigment measurement machines are linked to a central host. In response to a patient lacking a desirable level of macular pigment, the method further includes providing the patient with a recommendation for a first daily dosage of zeaxanthin (or other macular-pigment enhancing formulas) to increase macular pigment to the desirable level over a period of time. In response to a patient having a desirable level of macular pigment, the method includes providing the patient with a recommendation for a second daily dosage of zeaxanthin (or other macular-pigment enhancing formulas) that is less than the first daily dosage. The method also includes periodically transferring the information to the central host from the plurality of locations.

The method can also be considered a method of addressing vision problems in humans, comprising the acts of obtaining information from patients at multiple locations over a period of time, wherein the information includes macular pigment data obtained via a macular-pigment measurement machine at the locations. The plurality of macular-pigment measurement machines are linked to a central host and the information also includes specific patient information allowing patients to be placed in a plurality of subgroups of an overall population of patients. The method includes storing the information at the central host and, after the obtaining and storing, identifying a first patient at one of the multiple locations as being a member of a first one of the plurality of subgroups. The method includes retrieving, from the central host, macular-pigment-density data corresponding to the first one of the plurality of subgroups and displaying the displayable information to the first patient at the one of the multiple locations.

The present invention also includes a method of addressing vision problems in a population of humans. The method comprises the acts of obtaining information from patients at multiple locations, wherein the information includes macular pigment data obtained via a macular-pigment measurement machine at the multiple locations. The plurality of macular-pigment measurement machines are linked to a central host. The method further includes transmitting the information from the multiple locations to a central storage device associated with the central host, and on a periodic basis (e.g., not more than one month, one week, or even on day) transmitting specific sets of analyzed data from the population to the multiple locations. Alternatively, the transmitting of specific sets of analyzed data to a certain location may be simply in response to a request made from that certain location.

The present invention also includes a method of conducting a study that analyzes an existing recommendation for eye health. The method comprising the acts of obtaining information from patients at multiple locations, wherein the information includes eye-health data obtained via measurement machines at the multiple locations. The method includes electronically transferring the information to a central host that is linked to the multiple locations, and analyzing the information at the central host to develop a modified recommendation that modifies the existing recommendation. Finally, the method includes transmitting the modified recommendation to the multiple locations. As one example, the modified recommendation may be an intake of a certain macular-pigment enhancing formula to be recommended to the entire population or a sub-group of the population.

The present invention can also be considered an eye health measurement and storage system. The system comprises a plurality of macular-function measurement machines and a central host. The plurality of macular-function measurement machines measure macular function in humans. Each of the macular-function measuring machines includes a device for receiving macular function data from a patient, at least one data transfer port, and at least one processor that enables the transfer of the macular function data from the transfer port. The central host is coupled to the transfer ports on each of the plurality of computers. The central host includes a processor adapted to (i) store the patient data in a storage device and (ii) transmit macular-function study data to test locations associated with the plurality of macular-function measurement machines.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 1 illustrates the chemical structures of zeaxanthin and lutein (with an arrow pointing out the misplaced non-conjugated double bond in one end ring of lutein), and beta-carotene (a similar carotenoid that does not contain any oxygen molecules or hydroxy groups).

FIG. 4 illustrates a display associated with the computer of FIG. 3 for inquiring information from a patient.

FIG. 5 illustrates a display associated with the computer of FIG. 3 for confirming the results of an MPOD test.

FIG. 6 illustrates a display associated with the computer of FIG. 3 for confirming, at a later date, information from the patient specified in FIGS. 4-5.

FIG. 7 illustrates a display associated with the computer of FIG. 3 for confirming the results of an MPOD test taken at a later date.

DETAILED DESCRIPTION

Figure 2:
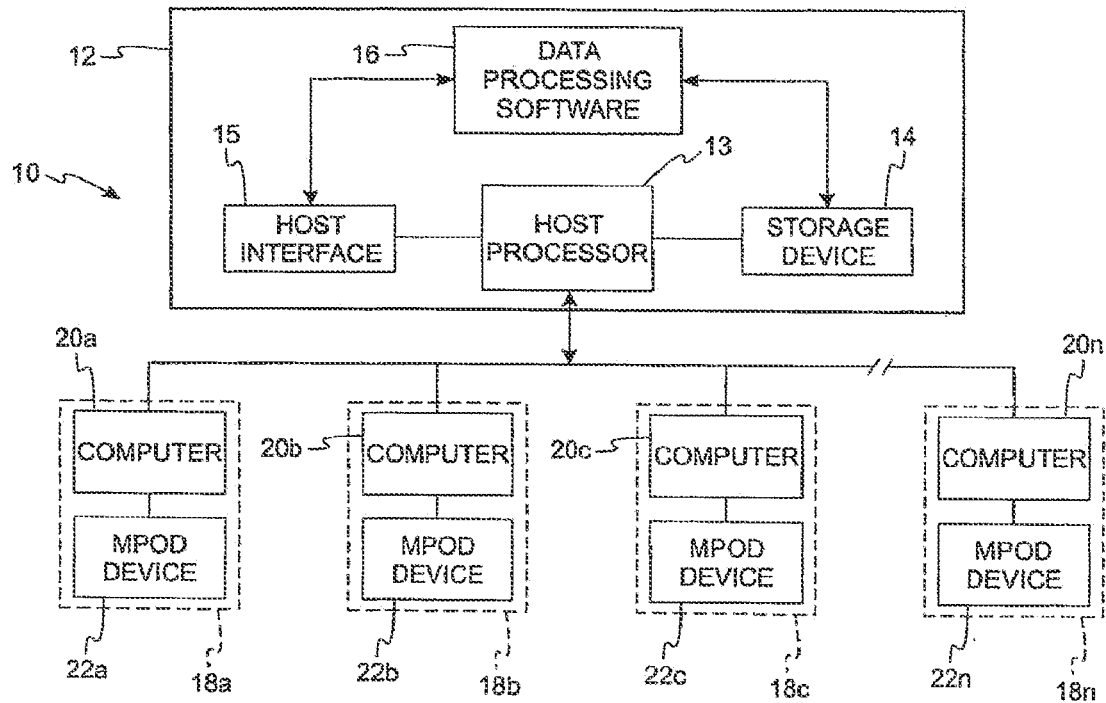
FIG. 2 illustrates an eye-health data gathering system.

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. As summarized above, this invention discloses and utilizes a distributed computerized system, and a business method that uses and depends upon the computerized system.

The distributed computerized system comprises hardware and software combinations that eventually will be installed in numerous (perhaps thousands) locations across the nation and around the world. The primary locations for such installations will be the "front line" eye care offices, such as where optometrists work, at other readily accessible locations such as shopping malls, retirement homes, etc., and at events such as fairs, conferences, meetings, etc. Such "front line" eye care specialists are the first (and often the only) eye care specialists most people will ever see. The distributed computerized system allows for macular pigment measurements to be taken quickly and with little effort on the part of the patient. The data is useful for many reasons, such as allowing the specific patient to determine the effects of certain nutritional supplements, and allowing the collection and analysis of data for a large scale population.

Referring to FIG. 2, the system 10 includes a host 12 that has a central processor 13 and a central storage device 14. The host 12 also includes a host interface 15 in which a host operator or analyst is permitted to review information that has been collected by the host 12, analyze the information, or send specific information throughout the system 10. Preferably, the host 12 included data-processing software 16 for allowing the host operator at the host interface 15 to access the data in the storage device 14 and analyze the data. The host operator can also make certain "packets" of data derived from data-processing software 16 available throughout the system 10 so that the patients and front-line eye specialists have access to important information, allowing them to understand the collected data regarding the eye study within the system 10 and to help them make important decisions for the patient. One example of a data packet focused on a certain sub-group of the population is show below in FIGS. 10-11.

The host 12 is coupled to a plurality of remotely located macular-pigment-measurement modules 18, each of which includes a computer 20 and a MPOD device 22 for measuring macular pigment density in a patient. It is contemplated that the system 10 will include macular-pigment-measurement modules 18a, 18b, 18c, . . . 18n, when the number "n" is preferably very large, such as in the hundreds or thousands.

Within each macular-pigment-measurement module 18, the MPOD device 22 is used to measure the patient's macular pigment density through one or more techniques, as described below. Each computer 20 is used for interfacing with the patient, a local operator, and/or a front line eye-specialist. Each computer 20 is additionally used to interface with the host 12 and pass information to and from the host 12. As one example, information that is sent from the computer 20 to the host 12 may include patient information, including macular pigment densities. As another example, information being sent from the host 12 to the computer 20 may include data about a patient that was input at a different location, but stored in the storage device 14, or statistical analysis of which eye supplements have been efficacious (for all patients or subgroups of patients) based on large scale data collected by the host 12 and analyzed by the storage device 14. More details of this type of data transfer will be discussed below, especially with respect to FIGS. 4-11.

In one preferred embodiment, the host 12 conducts a data-compiling function that uses the Internet or other means to gather and compile, from the numerous computers 20, the data that has been gathered by the front-line eye specialists and patients. The relevant data preferably should include: (i) pre-treatment data, such as age, gender, baseline macular pigment density levels, eye and health status, any history of smoking, diabetes, or other relevant medical issues, etc.; (ii) data on any zeaxanthin and/or lutein supplements or other eye supplements that are have been previously taken or have been prescribed, recommended, or sold to the patient; (iii) any changes in macular pigment levels that are detected by retesting, over a span of time after supplement usage has commenced; and, (iv) epidemiological data that tracks the development of macular degeneration, cataracts, changes in visual clarity, and other eye changes or disorders over a span of time. In addition, the business method that centers around the system 10 involves steps and incentives (such as described below) to encourage front-line eye specialists and their customers to participate in the process.

Figure 10:
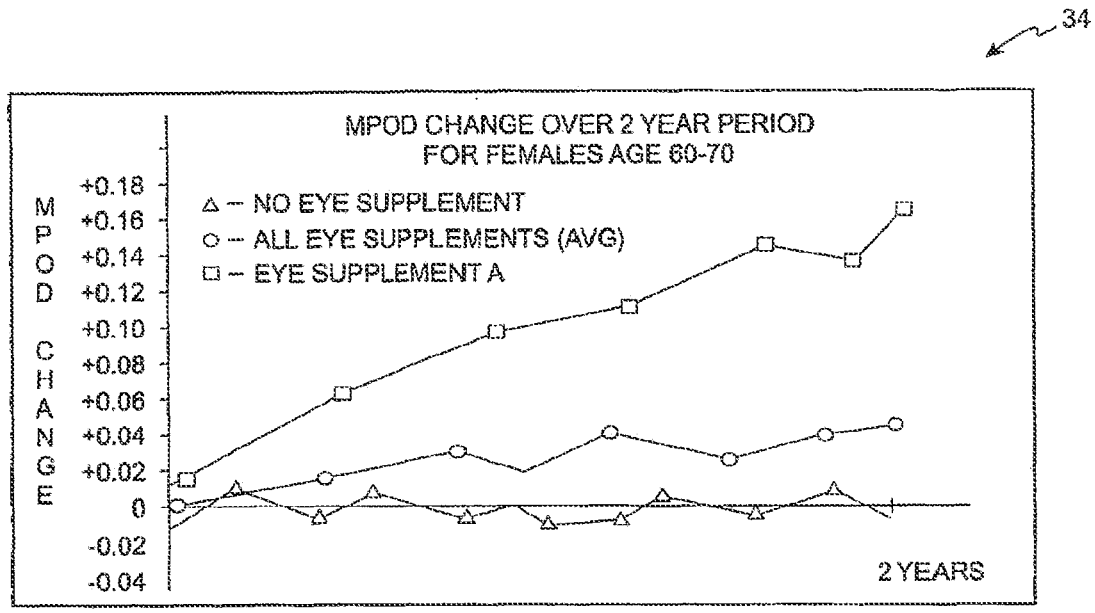
FIG. 10 illustrates a display associated with the computer of FIG. 3 for confirming the results of an MPOD tests for a group of patients.
Figure 11:
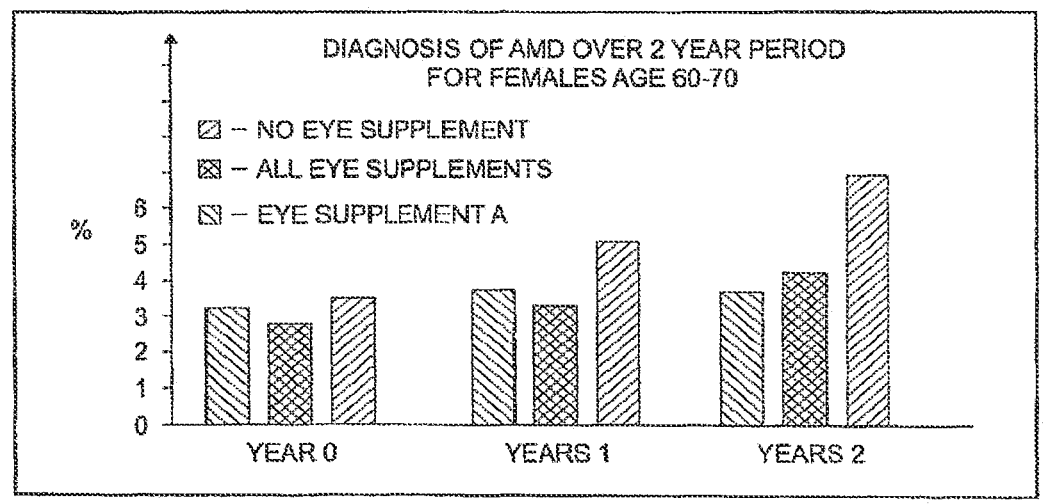
FIG. 11 illustrates a display associated with the computer of FIG. 3 for confirming the results of an MPOD tests for a group of patients.

The host 12 includes a centralized processor 13 with appropriate statistical or other analytical software, that processes and analyzes all of the data that have been gathered from numerous modules 18 in ways that will reveal trends and results from various supplement treatments, in various categories of patients. This will allow analysts at the host interface 15 to determine "best practice" recommendations for various categories of patients. It will also enable analysts to continually monitor additional data that are being gathered, thereby enabling "feedback" that is continually or periodically being sent to the modules 18 that will lead to refined and improved "best practice" recommendations for differing categories of patients. The feedback will include data "packets" derived from data-processing software 16, an example of which is shown in FIGS. 10-11.

There are various types of MPOD devices 22 that could be used in the system 10 of FIG. 1. Seven different general groups of exemplary MPOD devices 22 will be discussed— (i) scanning laser ophthalmoscopy, (ii) reflectometry, (iii) "flicker photometry" (also known as "heterochromatic flicker photometry", or HFP) (iv) autofluorescence spectrometry, (v) Raman scattering, (vi) modified fundas camera photography, and (vii) anomalscope. Each of these MPOD devices 22 can be coupled to the associated computer 20 and provide information concerning the patient's macular pigment density. Each of these MPOD devices 22 has its own combination of costs, convenience, accuracy, and drawbacks. Unlike "post-autopsy" methods for chemically analyzing retinal tissue that has been removed from the eye of a corpse, these non-invasive methods of the MPOD devices 22 use light, photography, or similar means. The results usually are expressed as "optical density", rather than as concentrations. The acronym "MPOD" is often used, to represent "macular pigment optical density." It is a dimensionless number, sometimes expressed in terms of "density units." With regard to Raman Scattering in particular, its results are expressed in the form of Raman Counts, which is not a dimensionless number.

To provide a frame of reference, at the current time, various published articles tend to suggest that MPOD values, as measured by flicker photometry, of about 0.4 or higher tend to be reassuring, while MPOD values less than about 0.3 (and even more especially, less than about 0.2) tend to indicate a below-normal amount of macular pigment. However, those numbers have not yet reached a level of consensus acceptance, and questions arise about how measurements made by different methods actually compare against each other. As such, whichever type of MPOD devices 22 are used within the system 10, the outputs are preferably calibrated so as to provide a consistent level of results over time. Depending on the method used, the MPOD values of what is "normal" may be different, and the present invention assumes the MPOD devices 22 have undergone calibration to develop a value of what is "normal," "above-normal," and "below-normal."

These methods and machines are surveyed in "In vivo Assessment of Retinal Carotenoids: Macular Pigment Detection Techniques and Their Impact on Monitoring Pigment Status," by Celentano et al (2002), a review that provides numerous citations to articles describing each of the main classes of machines. Other articles, such as "Influence of Lutein Supplementation on Macular Pigment, Assessed With Two Objective Techniques" by Berendschot et al (2000), and "Macular Pigment Density Measured By Autofluorescence Spectrometry: Comparison with Reflectometry and Heterochromatic Flicker Photometry," by Delori et al (2001), compare the accuracy of various techniques against each other. These three articles are incorporated by reference in their entireties.

Scanning Laser Ophthalmoscope (SLO) A method called "scanning laser ophthalmoscopy" (SLO) is a somewhat complex and expensive MPOD device 22, and may require a highly trained operator. Briefly, SLO uses two different lasers to create two different digitized photographs of the macula, in two different "passes." One laser uses a blue or blue-green wavelength, which is efficiently absorbed by the macular pigment. The extensive absorption of the blue-green light by the macular pigment leads to low levels of light being reflected and emitted by the macular tissue, in ways that will cause the emitted light to reach a specialized camera that is positioned directly in front of the eye. The other laser uses a different color (such as red) that is not absorbed by the macular pigment. Non-absorbance of laser light having this color, by macular pigment, leads to higher levels of reflected and emitted light reaching the camera. Both of those two lasers, with differing wavelengths, are used to create digitized photographs called "macular pigment maps". A processor is then used to compare the two digitized maps against each other. Large differences between the two maps indicate high concentrations of macular pigment; smaller differences indicate lower levels of pigment.

Berendschot's "Influence of Lutein Supplementation on Macular Pigment, Assessed With Two Objective Techniques" (2000), which is herein incorporated by reference in its entirety, indicated that over the course of time, when subjects participating in a lutein supplement trial were analyzed repeatedly by SLO measurements, the "spread" or "scatter" of the data indicated that SLO was accurate to a level of about ±10% of the value indicated by a measurement. That was the highest level of accuracy that could be achieved by any of the MPOD machines that were tested by Berendschot et al (1999 & 2000). However, at the current time, SLO machines are fairly expensive and complex, which may make their use a bit more difficult for populating the offices of hundreds of front-line eye specialists. SLO machines and methods are described in more detail in articles, such as Elsner et al 1998, which is herein incorporated by reference in its entirety.

Reflectometry. Another approach to measuring MPOD levels is usually called "reflectometry". This type of MPOD machine 22 also uses at least two different excitatory lights having two different wavelengths.

Some forms of reflectometry use two different wavelengths, which will include (i) a blue or blue-green wavelength that is absorbed by macular pigment, and (ii) a red or other wavelength that is not absorbed by macular pigment. Other forms of reflectometry (usually called "spectral" reflectance) can measure a retinal reflection levels over an entire range or spectrum of wavelengths, in a way that generates a curve which depicts the results across the entire spectrum.

In either case, a light beam with a known intensity is directed into the eye, and the intensity of any light that is reflected by the retina, and that emerges from the eye and reaches a photodetector, is measured. Instead of creating a map or photograph, this analysis merely creates a number for each wavelength that is measured. This number is usually expressed as a ratio, in which the amount of light reflected back from the retina is divided by either: (i) the total amount of light that was sent into the eye, or (ii) the amount of light that was absorbed inside the eye, calculated by subtracting the amount of emerging light, from the amount of light sent in. The number that corresponds to a red or other non-absorbed wavelength establishes a "baseline physiology" level for an eye, which can vary, depending on factors such as lens density, age and condition of the retinal tissue, etc. The number that corresponds to a pigment-absorbed blue or blue-green wavelength is then compared against the number for the non-absorbed wavelength. This generates a numerical indicator of the macular pigment density in that eye.

Continuing the comparative analysis mentioned above, Berendschot et al (1999 2000) reported that in their lutein supplement trial, data generated by spectral reflectance indicated that their reflectometry measurements were accurate to a level of about ±17% of the value indicated by a measurement (which was less accurate than the results obtained by the SLO method).

One promising reflectometry machine has been developed by a group (Dirk van Norren, Jan van de Kraats, Suze Valen, & Tos T. J. M. Berendschot) at the University Eye Clinic Maastricht in the Netherlands. In a poster board presentation at a meeting for The Association for Research in Vision and Ophthalmology (ARVO) in April 2005 in Fort Lauderdale, Florida, entitled "Fast and Objective Measurement of Macular Pigment with Natural Pupil," (incorporated by reference in its entirety), the developers describe a reflectometry MPOD machine 22 that does not require eye dilation. The written form of the presentation is incorporated by reference in its entirety.

Flicker Photometry A third method of determining MPOD values is usually called "flicker photometry" (also known as "heterochromatic flicker photometry", or HFP). It is sometimes called a "psycho-physical" method, since a person being tested must indicate when he sees, perceives, interprets, and believes something has happened. Various types of flicker photometers have been developed, and are described in U.S. Pat. No. 5,936,727 (Bone et al), U.S. Pat. No. 6,017,122 (Bone et al), and U.S. Pat. No. 6,315,412 (Snodderly et al), and in articles such as "A Practical Method of Measuring Macular Pigment Optical Density," by Wooten et al (1999), "A Portable Instrument for Measuring Macular Pigment with Central Fixation," by Mellerio et al (2002), and "Macular Pigment Measurement by Heterochromatic Flicker Photometry in Older Subjects: The Carotenoids and Age-Related Eye Disease Study," by Snodderly et al (2004). These patents and articles are incorporated by reference in their entireties.

In this type of MPOD device 22, electrical and/or mechanical components can be used to create "pulsatile" light patterns that alternate back and forth between a blue color, and a green color. In one design that uses electronic means, a flicker photometer tightly packs together a number of "light-emitting diodes" (LED's) in a small cluster. Some MPOD devices 22 involving flicker photometer use a single small circle (such as less than about 5 mm or ¼ inch in diameter), while other machines use more elaborate patterns (for example, Snodderly et al 2004 appears to describe a circular cluster surrounded by an annular cluster, for developing a "spatial profile"). LED's can respond very rapidly (such as hundreds or thousands of times per second) to changes in current passing through them. Some of the LED's in the cluster will emit light at a blue or blue-green wavelength that is absorbed by macular pigment, while other LED's in the cluster will emit light at a different wavelength (usually in a green or green-yellow range) that is not absorbed as well by macular pigment. Using an electronic circuit, the two different sets of LED's can be excited ("lit up") in a manner that causes their light emissions to alternate back and forth between the two colors, at a frequency that usually can be varied, but that typically alternates back and forth between two different profiles (or levels, conditions, etc.), over a range of about 10 to about 50 pulses per second.

A different design, disclosed in U.S. Pat. Nos. 5,936,727 and 6,017,122 (Bone et al), uses a rotating mechanical plate or similar device, with an opening (which can be called a shutter, aperture, etc.) that passes over both a blue and a green light source, in a way that allows one color or the other to pass through the aperture. The speed of rotation of the shutter plate can be varied, causing the frequency of the light pulses to vary. Flicker photometers that are believed to embody this design are being offered for sale by a company called Macuscope (www.macuscope.com).

Regardless of which design is used, if the frequency of the pulsation is set at a high rate (such as about 50 cycles per second, or "hertz" (hz)) and a suitable intensity, the macular pigment will absorb the blue light in ways that prevent a viewer from detecting any noticeable "flickering" (or pulsating, etc.) appearance, in the light emissions having two different colors. A rapid pulsating frequency prevents the macula from distinguishing between the two different colors, causing a rapidly pulsating light source to have a steady appearance.

However, because of certain aspects of photoreceptor physiology and chemistry, when the frequency of the pulsating color changes is reduced in a gradual and controllable manner, a threshold level will be reached where the viewer notices that the light begins to appear unsteady, in a flickering manner. Alternately, if the frequency of the pulses is held at a suitable rate (such as about 15 hz, for most people), but the intensity of one or both of the light emissions is gradually increased, a threshold level will be reached where the viewer notices that the light begins to flicker.

When the threshold or transition stage is reached, during a slow and gradual ramping-type change of the frequency and/or intensity of the pulsatile light emissions, the viewer will take some action to indicate that his or her threshold level has been reached. For example, in some machines, the viewer can turn a knob that adjusts the frequency or intensity of the pulsating blue and green light emissions, until the flicker disappears and the blue-green dot appears steady and constant. In other machines, the viewer can press a button as soon as he or she notices that the colored dot has begun to flicker.

Regardless of which type of action is taken by the user, the frequency, intensity, or other gradually changing trait of the electrical pulses that are being sent to the diodes, at that threshold level, will be processed or recorded by the machine.

Since higher concentrations of macular pigment lead to higher absorption of blue light, a lower sensitivity to a flickering appearance is correlated with higher macular pigment concentrations. As a result, flicker photometry machines can correlate a "threshold" flicker level for any particular patient (as measured above, using a slow and gradual "ramped" alteration of frequency or intensity levels) with the macular pigment density, for that patient.

Continuing the analysis mentioned above, Berendschot et al (1999 & 2000) indicated that the "spread" or "scatter" of the data that was generated by flicker photometry indicated that their those measurements were accurate to a level of only about ±71% of the value indicated by a measurement. This was less accurate than either SLO or reflectance measurements. However, it is believed that higher levels of accuracy and repeatability can be achieved with more recent and improved machines that have been developed in the last 5-6 years since Berendschot et al (1999 & 2000) publications.

As one example, in the system developed by Snodderly et al, an optimal flicker frequency should be determined, for each patient using the machine. After that optimal frequency has been determined for a particular patient, it is then used for subsequent testing of that patient.

In an alternate design created by Dr. Ian Murray et al, the intensity of the pulsating blue and green emissions is held constant, while the frequency begins at a high rate and is gradually lowered. As soon as the patient detects a flicker, he or she presses a button, which terminates the cycle and commences a new cycle, beginning once again at a high frequency. By minimizing the amount of apparent flicker that the retinal neurons and the vision centers of the brain must process, this approach helps minimize certain types of "neural adjustment and accommodation" mechanisms that the eye and brain normally use, which otherwise can lead to reduced accuracy, in subsequent "runs" that are done within a short time frame. This type of MPOD device 22 is discussed in a patent application in the United Kingdom, GB 0507430.7, which is incorporated by reference in its entirety.

Autofluorescence Spectrometry. Methods and machines also have been developed for carrying out a technique that exploits another age-related factor. By the time a normal person reaches the age of sixty, he or she will have accumulated some levels of two types of cellular debris, called drusen and lipofuscin, in the structural layers of the eye behind the retina. Those types of debris are well-known, and are discussed in detail in numerous articles.

One of those two types of debris, lipofuscin, is fluorescent. If excited by light with blue wavelengths (which are absorbed by macular pigment), lipofuscin will fluoresce, which means it will emit light having substantially longer wavelengths that are not absorbed by the macular pigment.

To exploit that fact, the MPOD device 22 using autofluorescence spectrometry (also called fundus autofluorescence) sends in a beam of blue light into the eye. Depending on the density of the macular pigment, some portion of the blue light that enters the eye will be absorbed by the macular pigment, and it will never reach any lipofuscin deposits that are located behind the retinal layer. The unabsorbed remainder of the blue light beam will pass through the macular pigment and the retinal layer, and it will reach the structural layer behind the retina. That unabsorbed blue light which reaches the structural layers will cause the lipofuscin deposits begin fluorescing, which causes them to emit light at a substantially longer wavelength. Fluorescing light that is emitted by the lipofuscin will not be absorbed by the macular pigment; therefore, some portion of that fluorescing light will travel back out of the eye, where it will reach a camera or photodetector that measures its intensity.

Therefore, if a person has a high level of macular pigment, most of the blue light will be absorbed before it can reach the lipofuscin, and the levels of fluorescent emissions by the lipofuscin deposits will be low. By contrast, if a person has a low level of macular pigment, more blue light will reach the lipofuscin, and the levels of fluorescent emissions by the lipofuscin will be higher. This enables the levels of macular pigment to be measured. These types of autofluorescence measurements are discussed in articles such as Delori et al 2001 and "Fundus autofluorescence imaging compared with different confocal scanning laser ophthalmoscopes" Bellmann et al (2003), which are hereby incorporated by reference in their entireties.

Raman Scattering. Another method of measuring MPOD relies on a phenomenon known as "Raman scattering" of light, described in "Resonance Raman Measurement of Macular Carotenoids in the Living Human Eye," Bernstein et al 1998. A full description of Raman scattering is beyond the scope of this application, and is not essential for an understanding of this invention. However, a brief overview can help readers understand it, if they choose to dig deeper.

Nearly any complex molecule that has multiple bonds (especially unsaturated bonds) can cause some degree of Raman scattering. While it is a weak phenomenon, it can be measured by sufficiently powerful or precise instruments, or under conditions of relatively strong excitation. Therefore, measuring the exact patterns of the shifts in wavelengths, caused by Raman scattering of a particular known light source by some particular gaseous or liquid mixture, can provide useful clues about what is in the mixture.

Since zeaxanthin and lutein (the two macular pigments) are complex molecules with multiple double bonds, they each cause their own characteristic types of Raman scattering, with slightly shifted wavelengths. Those characteristic scattering patterns can be used to determine the concentrations of zeaxanthin and lutein, in human maculas.

Since Raman scattering is a fairly weak phenomenon, a powerful light must be shone directly into the eye. Early tests suggested that the light may be uncomfortably bright for patients. However, using some type of Raman scattering MPOD device 22 may be possible as development of this type of technology continues.

Modified Fundas Camera and the Anomalscope. The modified fundas camera utilizes multiple wavelengths and filters to measure the macular pigment density. An anomalscope may also be used to measure macular pigment density.

Figure 3:
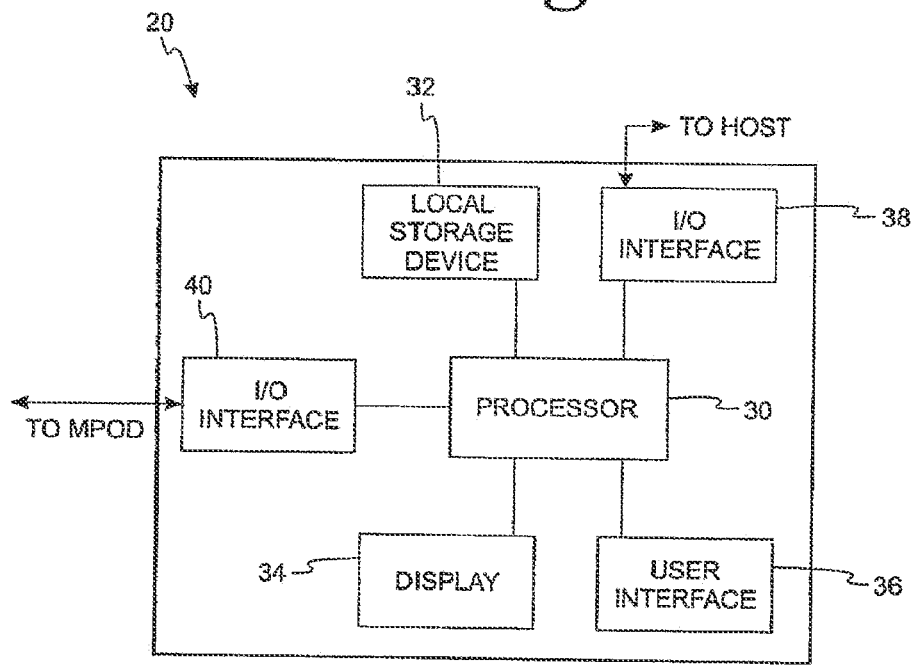
FIG. 3 schematically illustrates a computer used in the eye-health data gathering system of FIG. 2.

Referring now to FIG. 3, the computer 20 is schematically illustrated in more detail. The computer 20 includes a processor 30 for executing the various instructions related to the overall functions of the computer 20. The processor 30 is coupled to a local storage device 32, a display 34, and a user interface 36. The local storage device 32 (one memory device or several memory devices) stores the various instructions that allows the computer 20 to interact with the MPOD device 22, to interact with the host 12, and to receive inputs and provide outputs to an individual operating the computer 20. Although the display 34 is shown as been a part of the computer 20, it should be understood that the display 34 can be one of many types of output devices such as CRT screens, flat screens, plasma screens, etc. fr that are coupled to the processor 30. The user interface 36 can be in the form of a keyboard, a voice recognition system, a touch screen overlying the display 34, and/or other types of input devices allowing the user to enter information to the computer 20.

The user interface 36 may also receive information a biometric reading device for recognizing a distinguishable physical attribute of a patient so as to identify the operator for providing access to the computer 20. The biometric reading device may be contacted by the hand of the operator to read the geometry of the hand or the fingerprints on one or more of the fingers. After the biometric reading device scans the information, the processor 30 (or a remote processor at the host 12) performs a comparison to determine the identification of the operator at the computer 20. Additional information regarding fingerprint scanning or hand geometry scanning is available from International Biometric Group LLC of New York, NY.

Other biometric identification devices can be used and coupled to the operator interface 36. For example, a microphone can be used as the biometric identification device so that an operator can be recognized using a voice recognition system. In such a system, a patient claims an identity, which is recorded, and his or her voice-print is matched to a voice-print on file to verify the operator's identity. Further, the computer 20 may include a biometric identification device that scans the retina or the iris for identifying the patient. Additional information regarding iris or retinal scanning is available from International Biometric Group LLC of New York, NY The MPOD device 22 may also incorporate a retinal scanner for identifying the patient.

The computer 20 includes an input-output interface 38 allowing the computer to be coupled to the host 12. Similarly, the computer 20 also includes an input output interface 40 allowing the computer 20 to be coupled to the MPOD device 22.

In one preferred embodiment, the computer 20 is a conventional desktop or laptop computer, as already found in nearly in place of business, which has been modified by loading software into it that will also permit that computer to function as a unit within the system 10. In some regards, the MPOD device 22 that measures macular pigment may be considered a "computer peripheral" that interacts with the computer 22 in an office of the front line eye specialists. The input-output interface 40 is preferably a USB port (USB-1 or USB-2 interfaces), which is ideally suited to provide this type of interface to a peripheral device. The USB system has been adopted worldwide, and most modern computers are sold with at least two, frequently three, and often four USB slots. In addition, small and inexpensive external routers or hubs can be plugged into any USB slot, to convert that slot into multiple additional USB slots. Nevertheless, it should be recognized that other data transfer protocols are available, and can be used if desired. Such data transfer interfaces that can be used with the input-output interface 40 of the computer 20 include the "Firewire" (also called the IEEE 1394 standard), wireless systems such as "WiFi" and "Bluetooth", and other communication protocols (such as the X10 system) that transmit data signals that are "layered" on top of alternating current power supplies.

The input-output interface (or interfaces) 40 enables the computer 20 to interact and exchange data and/or commands with one or more types of external devices that can be plugged into the computer 20, via a cable or similar interface, as described below. In home and office use, computer peripherals include printers, digital cameras, video cameras, joysticks or other controls for games, audio equipment such as microphones, telephones, musical devices, etc. In laboratories, most types of analytical devices (often called "instruments") such as chromatographs, spectrometers, photodetectors, etc., have been adapted to convert any measurements into digital signals that can be sent to a computer. Such devices usually contain at least one microprocessor (i.e., an integrated circuit that has been loaded with software code that allows the device to be activated and controlled by commands from a computer). In one basic type of system architecture, the processor 30 within the computer 20 is considered the "master" while the processor within the MPOD device 22 is considered the "slave" that performs the functions dictated by the processor 30.

Software that allows for the functioning of data transfer between MPOD device 22 and the computer 20 is located within the MPOD device 22 and the computer 20. In other words, the MPOD 22 includes software allowing it to operate so as to take measurements from the patient and software that provides for communication of the data to the computer 20. And, the software in the computer 20 allows it to receive information from the patient via the user interface 36, receive data from the MPOD device 22, and store that data in the local storage device 32 in a file associated with the patient. As discussed below, the patient-specific data files are preferably transferred on a periodic basis to the host 12 for storage in the host storage device 14. The software for the computer 20 is written for a particular type of operating system that runs the computer 20. Because of the dominance of "WINDOWS XP" (trademark of Microsoft Corporation) and other "WINDOWS" varieties as the operating system for computers 20 used in offices of the front line eye specialists, any software written for the computer 20 is often compatible with most existing systems such as the WINDOWS XP system. If desired, the software also can be "ported over" to other systems, such as computers that are running Linux and/or MacIntosh software. Accordingly, skilled programmers who specialize in writing software for computerized peripherals that interact with computers are readily available and can create software packages that allow the MPOD device 22 and the computer 20 to interact.

As mentioned above, the computer 20 in the front-line eye specialist office must have the input-output interface 38 to allow the computer 20 to transfer data to the host 12 that will compile data from numerous offices. The input-output interface 38 can be provided most conveniently by using the Internet. This can be done via either (i) a conventional modem, which allows data to be sent or received via a conventional telephone connection, or (ii) "Ethernet" ports and cables, which allow high speed (often called "broadband") data transfers. Both types of hardware interfaces are well known, and are contained in nearly all desktop, laptop, or notebook computers. Software for allowing such data transfers is also well known, and includes Internet browser programs (e.g., Microsoft's Internet Explorer, Mozilla's Firefox, and the America Online system), e-mail software that allow files to be sent as attachments (e.g., Outlook, Eudora, and AOL), and stripped-down systems that have few graphical interface requirements, such as "ftp" (file transfer protocol) software that can be run in Windows, Linux, DOS, and other systems.

As will be recognized by those skilled in the art, convenient and automated data transfers that do not require any individual attention (unless a malfunction occurs) can be made within the system 10 from the computers 20a-20n (FIG. 2) to the host 12 by means of an Internet website. An entire website can be dedicated to that purpose; alternately, one or more web "pages" or options can provide that function as part of a larger website. The coding that is required to create that type of website functionality is well within the skill in the art among specialists who design and create web pages, and dozens of different software packages are available for that type of coding (Microsoft's FRONTPAGE and Macromedia's DREAMWEAVER are two examples of software packages that help programmers create websites that can interact with other computers).

The host 12 has the desired functionality for receiving, storing, and processing thousands of data files that will be sent to it, presumably on a weekly, monthly, or quarterly basis, from hundreds or thousands of different computers 20. The host 12 can be considered a so-called "server" that has enough storage with the storage device 14 (one device or several storage devices) to function as a "holding tank" for the data, until the data is processed and handled in an appropriate manner. Such processing will include, for example, periodic creation of backup and/or transfer copies of the data, using storage systems such as portable storage medium (e.g. CDs).

File transfers from the computer 20 to the host 12 can be done by using automated routines that are comparable to sending an email with an attached file to a recipient. The computer 20 can be programmed to automatically send the data at any convenient time (such as, for example, once per week, every Tuesday morning, or once per month, on the second Tuesday of the month, as soon as the computer is turned on that morning). Designated target transfer times can be assigned and distributed among different participating computers 20a to 20n, to create relatively steady levels of transfers throughout a week or month, rather than having thousands of transfers at the same time. The computer 20 can be assigned to overnight hours with low traffic levels, such as between midnight and 6 am. If desired, more than one "server" at the host 12 can be used, and such servers within the host 12 can be located in different parts of the globe, such as one in Asia, one in Europe, and one in North America.

Each file transferred by the computer 20 can be given a coded filename that will make it easy to clearly identify the sources and dates of all such files that are received by the host 12. This can be done automatically by the software that runs on the computer 20. For example, the first "field" in each filename can contain 4 to 8 letters or digits, which will identify the specific computer 20 that sent the file. An arbitrary punctuation mark can be inserted next, to separate the first and second fields, and to ensure that only properly-named files will be sent to the standard folder or directory that receives those particular files, while any other files are sent to other folders or directories on the server. The next 6 to 8 digits can indicate the opening date of a file (such as using a DDMMYY sequence, where D, M, and Y are variables that correspond to a specific day, month, and year). Another arbitrary punctuation mark can set off the next field in the filename, and the last 6 to 8 digits can indicate the closing date of the file.

Other and/or additional file naming protocols can be used if desired. For example, a confirmatory digit can be added to the end of the filename, which will calculated by the computer as it creates the file name, in a way that causes the sum of all of the digits in the filename to add up to an arbitrary number (such as a multiple of ten, which must end in a zero). This type of system, to create a checking and confirming mechanism, is widely used in barcodes, ISBN numbers for books, etc.

While these types of file transfers can be automated and made simpler and more convenient by using websites and Internet resources, alternate and/or additional file transfer and data collection options can be provided and used, if desired. As one example, various types of computerized "polling" routines and options can be used. In one set of options, the host 12 can be programmed to directly and securely contact each computer 20 in a list of computers, either on a regular periodic basis, or if a scheduled file transfer has been missed by more than a fixed period of time (such as more than two days, a week, etc.). In another set of options, if a file transfer has not occurred within a certain period of time, a window can open automatically on the display 34 of the computer 20, stating that a file transfer needs to be made soon, and asking the operator for instructions to either activate a file transfer at that time, or to provide another reminder at some time in the future (such as an hour, day, or week later). These types of routines are used by various companies that handle business over the Internet, such as (for example) companies that provide anti-virus software for computers (e.g., McAfee™ Security), which must be updated regularly in order to remain effective. Such methods can be adapted for either of two classes of use: (i) to supplement regular and scheduled file transmissions to an Internet website; or, (ii) as part of a program that requires individual "polling contacts" to be established directly between two computers.

FIGS. 4-11 will now be described in more detail. Each of these figures relates to information that can be illustrated on the display 34 of the computer 20 within each module 18. As will be seen in the discussion below, the display 34 is useful for the patient who is having his or her macular pigment tested and the operator of the module 18 (e.g., an optometrist) who uses the computer 20 to learn more about a specific patient or results provided by the host 12 as to what nutritional supplements could be beneficial to his or her patients.

FIG. 4 illustrates an exemplary screen on the display 34 of the computer 20 for a new patient who is taking the macular pigment test for the first time. The computer 20 is requesting that the patient enter various bits of patient information 50 through the user interface 36 associated with a computer 20. The patient may enter this patient information 50 through a keyboard or touch screen overlying and associated with the display 34. The display 34 may also include a date field 52, with the date being entered by clock associated with the computer 20.

It must also be noted that the computer 20 may provide automated instructions that can help guide users through complex processes, or sequences of multiple steps. For example, digitized voice instructions as an output to the patient can be provided by a small and inexpensive speaker that can play a pre-programmed sequence of audio files (e.g. mp3 files that can be stored in the local storage device 32). Other types of computer files, in formats that have filename extensions such as .mov, .avi, or .vob (these and other video file types are familiar to those who work with computerized video files) can be used to play video segments that contain audio soundtracks. These files for assisting and instructing the patient can be stored on at the local storage device 32 of the computer 20. Alternatively, they can be stored in a peripheral device, or on a videotape, digital video disc (DVD), mini-disc, or any other suitable storage media that can be played on an electronic player (for example, small and portable DVD players, with screens ranging from about 7 to about 10 inches diagonally and with built-in speakers, are widely available at relatively low cost).

Within each patient's data file, the data will be organized into arrays of different "fields". This will be comparable to a table that contains columns and rows, with each row containing all of the relevant data from a specific customer or patient, and with each column assigned to contain a certain particular type of data. For example, the patient enters data in the manner shown in FIG. 4 so as to provide some or all of the following information for the patient's data file.

(1) a patient's identity, which can be identified by any of several means (such as a patient's complete name if the patient has given permission, a patient's initials (which can be supplemented by the patient's year or date of birth, to avoid potential conflicts), or an arbitrary coded number that is known only to the front-line eye specialist;

(2) the patient's age;

(3) the patient's gender;

(4) the patient's eye color; (in three or four crude categories that indicate blue, green, or brown, or one on a numerical scale that ranges from 01 to 99, which will be determined by using a color chart, with severe to moderate albinism in the 01-09 range, pale blue colors in the range of about 10 to 25, up to very dark brown eye colors in the 90's);

(5) the patient's general health status, which can include known risk factors such as diabetes, smoking, high blood pressure, etc.;

(6) the patient's responses to one or two brief questions asked about his or her diet, which will place the patient somewhere on a rough scale that will generally indicate high levels of salad and green vegetable intake at one end of the scale, and high levels of sugary, salty, or greasy snacks and fast foods at the other end of the scale;

(7) the types of drugs and/or nutritional supplements a patient was taking when the first macular pigment measurement was made;

(8) the patient's general eye health, indicating factors such as mild or severe far-sightedness, near-sightedness, or astigmatism, any problems relating to night vision, peripheral vision, color-blindness, glaucoma, etc., any presence of cataracts or lens implants, etc.;

(9) the patient's physical size, in weight and height, or body mass index;

(10) the patient's macular status, with any indicators of early-onset, middle-stage, or advanced problems in each eye, and also indicating any known family history, genetic analysis, or other indicators of various known eye disorders, such as Stargardt's disease, Best's disease, Batten's disease, Sjogren-Larsson syndrome, or macular degeneration;

(11) a patient's baseline (pre-treatment) levels of macular pigment, and also indicating both (i) how the macular pigment density was measured, and (ii) the degree of confidence that the optometrist had in that measurement, after witnessing the person who took the test;

(12) a coded number indicating whether the optometrist recommended that the patient should begin taking a nutritional supplement that contains zeaxanthin, lutein, or a zeaxanthin-lutein mixture;

(13) a coded number indicating whether the optometrist recommended that the patient should begin taking any other nutritional supplements, such as a general multi-vitamin supplement, an AREDS-type supplement with high dosages of anti-oxidants and/or zinc, etc.;

(14) a coded number indicating whether the patient purchased such supplements from the optometrist, or whether the patient purchased such supplements from any other source;

(15) any subsequently measured levels of macular pigment density, and the dates of such measurements;

(16) any onset or progression of macular degeneration, after the first measurement of macular pigment density.

Any or all of these data can be entered in the form of coded numbers that are associated with certain answers that are likely to be received from the patient. These data can be gathered and compiled in any way that is suited to the needs and working arrangements of a particular office. For example, some offices might prefer to have an optometrist enter all of the data; other offices might prefer to have a receptionist or other assistant gather at least part of the data, either from a brief interview with a customer, or from a worksheet that is filled out by a customer before the customer sees the optometrist. Still other offices might prefer to have at least some customers sit at the computer 20 and directly enter the appropriate information, which would then be reviewed and confirmed (and adjusted if necessary) by an assistant and/or the optometrist.

The patient information gathered in FIG. 4 can also be supplemented by any additional measurements and/or data that optometrists choose to gather that is helpful to his or her practice. Further, as the data analysis at the host 12 occurs over time, additional factual information about the patients may become relevant and the host interface 15 is used to request that each module 18 begin to gather that new fact. Further, the host 12 may download a new version of the software to the computers 20 that effectuates this change in collecting a new piece of factual information about the patients being tested at the modules 18.

In an alternative embodiment, items of the patient information are provided with a score or grade to help determine the patient's risk assessment for acquiring AMD. The following Table provides examples of the scores or grades.

| Factor | Score |
| --- | --- |
| age = 60-69 | +1 |
| age = 70-79 | +2 |
| age > 80 | +4 |
| gender, if female | +2 |
| eye color, if light | +2 |
| body mass index > 30 | +3 |
| smoking, if past smoker | +2 |
| smoking, if current smoker | +5 |
| family history of eye disease, cataracts | +2 |
| family history of eye disease, diabetic retinopathy | +3 |
| family history of eye disease, parent with AMD | +10 |
| family history of eye disease, sibling with AMD | +5 |
| current health history, cardiovascular problems, diabetics, or hypertension | +3 |
| diet, 2 daily servings of dark green leafy vegetables | −2 |
| diet, 4 daily servings of dark green leafy vegetables | −3 |
| diet, 2 daily servings of yellow/orange vegetables | −2 |
| diet, at least three weekly servings of cold water fish, such as salmon, tuna, or sardines | −2 |
| diet, daily intake of a multivitamin or an antioxidant mixture | −3 |
| extensive time in sun without adequate sunglasses | +2 |
| very sensitive to light | +2 |

After the patient or front-line eye specialist has entered the patient data, the computer 20 can quickly determine the patient's risk for becoming inflicted with AMD. The risk assessment score is then available to the patient and the front line eye specialist at the same time the MPOD test is being conducted. As an example, a risk assessment score of greater than X (e.g., +5) may automatically alert the front line eye specialist to a need for a certain type of macular-pigment enhancing formula. If the MPOD result for that patient is below average, then the risk assessment score and the MPOD result should be an influential piece of data that strongly suggests that the patient should be taking a macular-pigment enhancing formula, or preferably, a certain type of macular-pigment enhancing formula, which data within the system 10 indicates has been beneficial for similarly situated patients.

Another beneficial aspect of the real-time data gathering and analysis within the system 10 is that certain factors in the Table above may prove to be more important for predicting whether a patient may be inflicted with AMD. As an example, if the data gathered in the system 10 indicates that there is a strong correlation between patients who are very sensitive to light and diagnosis of AMD, the system 10 can send an updated Table to each of the modules 18a to 18n, to replace the Table listed above. As such, the updated Table may reflect a score of +4 for the category "very sensitive to light" instead of the +2 value listed above. Each computer 20 within the system 10 is then automatically updated for all future risk assessments of patients. The ability to provide simplistic, real-time updates to each testing module 18 is one of the primary benefits of the system 10.

FIG. 5 illustrates the display 34 on the computer 20 after the patient has conducted the test on the MPOD device 22.

In particular, the MPOD results 54 are shown to the patient along with information about what is an average, below average, low and good and MPOD test score. Additional information may instruct the patient on the next step, which may include a consultation with a doctor associated with the MPOD module 18, such as an optometrist.

FIG. 6 illustrates the display 34 for the patient during a follow-up visit to the module 18 and MPOD test. The patient is encouraged to repeat the tests over a period of time, especially if the patient had a low MPOD test result 54. The patient enters some type of patient identifier (name, login name, anonymous input, etc.) via the user interface 36 and the computer 20 is configured to illustrate on the display 34 the previously entered patient information. The patient is asked to confirm the information that he or she has entered in the previous visit. The patient may update the patient information 50, which has occurred here, in that the patient has now updated Question 10 to indicate the patient is now taking a daily eye vitamin. The date field 52 is also updated to include the date of this subsequent test.

In one preferred embodiment, the patient information associated with the patient is stored in the host storage device 14 and retrieved in response to the patient entering a patient identifier at the computer 20. In this way, the patient is able to take the same type of MPOD test at several different locations and is able to retrieve his or her patient information from any of the modules 18 connected to the host 12 within the system 10. Alternatively, the patient information may be saved locally at the front line eye-health office, such as in the storage device 32 of the computer 30 (assuming the patient visits the same location). In other words, the patient information may be stored in the local storage device 32 and that the host storage device 14. In this situation, depending on the methodology for transferring data to the host 12 from the modules 18, patient information can be updated or supplemented at the time the patient information is polled (e.g. periodic polling) from the modules 18.

FIG. 7 illustrates the MPOD results for a second test. As shown, when compared to the test results illustrated in FIG. 5, the patient experienced an increased macular pigment density, which is beneficial. One likely cause for the increased macular pigment density is the supplementation with the eye vitamin. While one aspect of the present invention concerns the overall system 10, it should be noted that supplementation with eye vitamins having a high content of zeaxanthin should drastically increase macular pigment density and, therefore, lower the patient's likelihood for being inflicted with advanced age-related macular degeneration.

Figure 8:
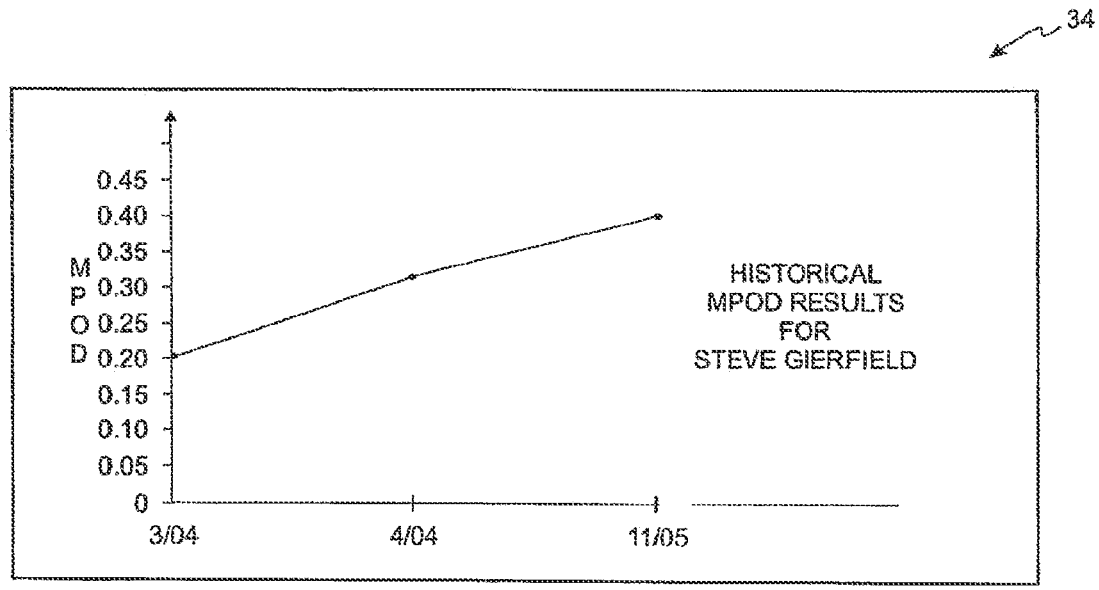
FIG. 8 illustrates a display associated with the computer of FIG. 3 for graphically describing the patient's MPOD test results.

FIG. 8 illustrates a graphical form of historical data output for the patient showing a significant increase in MPOD test results for the patient over a period of time. Again, allowing the patient to see the historical results of the MPOD tests helps to illustrate and reinforce the benefits achieved by altering some factor in the patient's life, such as supplementation with a certain type of eye vitamin. This type of graphical data shown on the display 34 of the computer 21 is also helpful for the front line eye specialist in understanding the past and current conditions in the patient's macula. It should be noted that FIGS. 7-8 are simply for illustration purposes as to how the display 34 will work and does not reflect the MPOD results of a real person.

Figure 9:
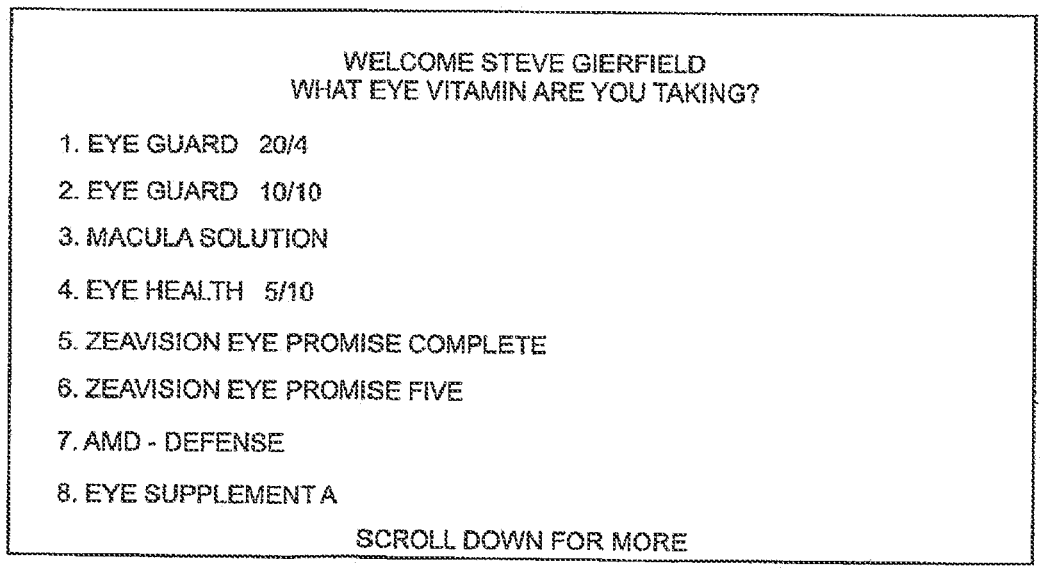
FIG. 9 illustrates a display associated with the computer of FIG. 3 for confirming the type of daily eye vitamins the patient is taking.

FIG. 9 illustrates a data input screen on the display 34 of the computer. This information may be displayed in response to a positive answer to the Question 10 in FIG. 4 or 6. In other words, if the patient indicates that he or she is taking an eye nutritional supplement, then the computer 20 may ask the patient which one of a variety of different types of eye vitamins are being taken. This type of inquiry may also be requested by an operator of the module 18 after the patient has indicated which nutritional supplement they are taking and the operator may enter a coded data entry corresponding to that nutritional supplement. In short, due to the type of data being collected related to the MPOD test results, it is preferred to learn about factual information about the patient's current eye vitamin supplementation.

FIGS. 10-11 illustrate the type of information that can be presented based on the patient information and MPOD data collected and analyzed from all of the modules 18 in the system 10. The host processor 13 along with an operator for guiding the host processor 13 via the host interface 15 (FIG. 1) develops various packets of useful information that are accessible to each of the modules 18. Considering the types of information that are entered by each of the patients, analyzing the data for certain population groups can be helpful for patients and those working in the front line eye offices. The analysis information based on the patient population derived at the host 12 can be periodically transmitted to the modules 18 (e.g., once a month, once a week, or once a day), providing the patients and the front line eye specialists with substantially real-time updated information. Alternatively, or in addition to the periodic transmission of analysis information, the analysis information can be transmitted to a certain module 18 based on the request of that certain module (e.g., upon the MPOD testing of a patient having certain characteristics associated with the patient's inputted information, and the analysis information is directed to a sub-group corresponding to those characteristics).

For example, as shown best in FIGS. 10-11, when a female patient in the age of 60 to 70 is having her macular pigment density checked for the first time, the patient and/or the operator of the module 18 can present information like that shown in FIGS. 10-11 on the display 34 of the computer 20. This information may be helpful to the patient as she makes choices about whether she should be taking some type of nutritional supplements. As such, this information can be presented to a patient after the patient has undergone the tests via the MPOD device 22 to learn that the patient's macular pigment density is low. Consequently, the present invention contemplates a methodology of (i) acquiring patient information at the time of the MPOD tests, (ii) based on the test results, retrieving information from the host 12 that is particularly useful for a specific patient based on his or her patient information (e.g., age, sex, smoker, etc), and (iii) displaying that information so that the patient can determine whether eye supplements have been found to be helpful, or not helpful, for similarly situated individuals who have undergone the same type of testing. The method further can be extended to displaying information pertaining to a particular eye supplement to the patient so that he or she can understand more about a certain eye supplement was found to be helpful for similarly situated individuals Like the data in FIGS. 7-8, the data in FIGS. 10-11 is for illustration purposes and does not reflect actual data that was gathered by the system 10

While FIGS. 10-11 show the results of some basic types of analysis of the data at the host 12, many types of analysis information can be performed by the host 12 on the large scale data that is retrieved from the various modules 18. Here are two examples of some of the analysis conducted by the data-processing software 16 at the host 12.

Comparing Types Eye Supplements. The data should allow a comparison of whether regimens of zeaxanthin, lutein, or zeaxanthin/lutein mixtures lead to comparable increases in macular pigment densities, or whether zeaxanthin-only (or zeaxanthin/lutein) supplements lead to faster and/or larger increases in macular pigment than lutein-only supplements. Such analyses can be subdivided, to analyze the general population while also analyzing specific subgroups, such as people with early-stage macular degeneration, abnormally low macular pigment, diabetes or diabetic retinopathy, a history of smoking or obesity, etc.

Comparing Dosage Levels. The data should provide for correlations that establish links between any or all of: (1) dosage regimens of zeaxanthin, lutein, or zeaxanthin/lutein supplements, (2) blood serum levels of zeaxanthin or lutein, to the extent that blood tests are performed; and (3) detectable changes in MPOD levels and any or all of: (a) stabilized or improved vision clarity; (b) other indicators of stabilized or improved vision, such as improved dark adaptation, improved glare handling or recovery, improved peripheral vision, etc; (c) other indicators of stabilized or improved retinal health, such as reduced progression of choroidal neovascularization or retinitis pigmentosis, improved recovery from eye injuries or infections, etc. The data should provide for other indicators of stabilized or improved retinal health, such as reduced rates of cataract growth or surgery, etc.

The results, trends, and conclusions that become apparent after the data have been gathered and analyzed by the system 10 will be highly useful in helping various groups of people (including optometrists, ophthalmologists, and other physicians, as well as government agencies, insurance companies, people who suffer from macular degeneration, diabetes, or other medical problems, and friends, family members, and other caregivers who help take care of elderly people). The data should reach better levels of shared insights and consensus understandings, concerning best practices for treating macular degeneration at various stages of severity and in various population groups, and for preventing it among the general population, especially among people who are known to be at elevated risk of macular degeneration.

Such "best practices" for either prevention or treatment cannot be known or predicted with certainty or reliability, prior to gathering and analyzing the relevant and useful data. However, as can be made clear by comparing the methods disclosed herein against the current plans for the AREDS-2 trial, the methods disclosed herein will create and provide a better method for gathering truly useful, helpful, and reliable date that will allow direct comparison of zeaxanthin against lutein, and against zeaxanthin-lutein mixtures. Zeaxanthin-lutein mixtures that are likely to be tested include (i) 5:1 ratios (i.e., lutein to zeaxanthin), as initially chosen by the people planning the AREDS-2 trial, to emulate the relative concentrations of those two compounds in circulating blood; or, (ii) 1:1 ratios (also called 50:50 ratios) which can roughly emulate retinal concentrations, and which can provide good mid-points in curves that will be generated from the data.

The design and conduct of the tests disclosed herein, and the creation, gathering, analysis, and reporting of the resulting data, are intended to be unbiased, in ways that will allow and encourage fair, direct, and revealing comparisons of zeaxanthin against lutein, and against zeaxanthin-lutein mixtures.

The Business Method of This Invention As mentioned above, the distributed computer system 10 of the present invention also enables the creation and implementation of a business method that is regarded as an integral part of this invention. The basic business method generally involves the following five steps:

(1) Placing multiple MPOD devices 22 that are designed and equipped (and which already contain software that will allow them) to interact directly with the computers 20 that are already found in offices of front-line eye specialists;

(2) Providing front-line eye specialists' with software that can be conveniently loaded onto their computers 20, which will allow computers 20 running such software to: (i) directly interact with and receive data from the MPOD devices 22; (ii) store and organize such data in properly formatted data files that contain relevant patient information, macular pigment data, other ocular and health data, and information on any zeaxanthin and/or lutein supplements that are actually purchased and used by such patients; and, (iii) periodically provide for the transfer of data files to a designated website or data-compiling computer associated with the host 12;

(3) Compiling and organizing the data files from the computers 20 at numerous different offices, into a coordinated compiled database at the host 12 that will allow analysis of the macular pigment data in ways that allow such data to be evaluated with respect to different population and subpopulation variables;

(4) Analyzing the compiled macular pigment data, to evaluate trends and reach scientifically-supported conclusions concerning the efficacy of eye supplements, and in particular, zeaxanthin and/or lutein supplements in preventing or treating macular degeneration;

(5) Transferring such compiled trends and related information (including information on trends and scientific conclusions concerning the efficacy of supplements for preventing or treating macular degeneration) available to the front-line eye specialists in ways that will help patients and front-line eye specialists to make intelligent and reasonable decisions that can help them avoid or treat macular degeneration.

The business method outlined above can be enhanced by also carrying out one or more of certain optional steps, as follows:

(1) Using the compiled scientifically-supported trends and related information to issue, publish, and publicize a set of "best practice" recommendations for eye supplementation, in ways that can be subdivided and adjusted as appropriate for various classes or subgroups of patients (such as, for example, patients who can be assessed and placed into one of the following four categories: (a) patients with apparently good eye health; (b) patients with diabetes and/or early indicators of macular degeneration; (c) patients with moderate-stage macular degeneration; or, (d) patients with advanced macular degeneration).

(2) Continuing to gather data from front-line eye specialists in the system 10, and using such data to continue to study any trends that are shown by the data, among different population groups, thereby creating a feedback loop that will lead to ongoing refinements and improvements in the "best practice" recommendations for various population groups.

(3) Periodically or intermittently publishing and publicizing any updates or adjustments to the "best practice" recommendations, preferably with assistance and support from government agencies, public health officials, consumer advocates, and not-for-profit organizations that work to help prevent or treat blindness; and (4) Providing, at the front-line eye specialist, a plurality of eye supplements that are provided to patients based on certain conditions. As an example, the patient is provided with a recommendation for a first daily dosage of zeaxanthin (or another type of macular pigment enhancing formula) to increase macular pigment to a desirable level over a period of time in response to having an undesirable macular pigment level. In the alternative, the patient is provided with a recommendation for a second daily dosage of zeaxanthin (or a second type of macular pigment enhancing formula) that is less than the first daily dosage time in response to having a more desirable macular pigment level. Such recommendations and sales can help ensure that health care recommendations from a skilled professional are actually followed by customers (especially elderly customers, who may be forgetful, or who may not be able to take all of the various steps that might be necessary to order something over the Internet or through similar channels). On-the-spot sale and delivery of nutritional supplements directly into the hands of a person who is suffering from a vision problem, and who needs such supplements in order to prevent serious worsening of his or her vision problem, is especially helpful, important, and proper.

Figure 12:
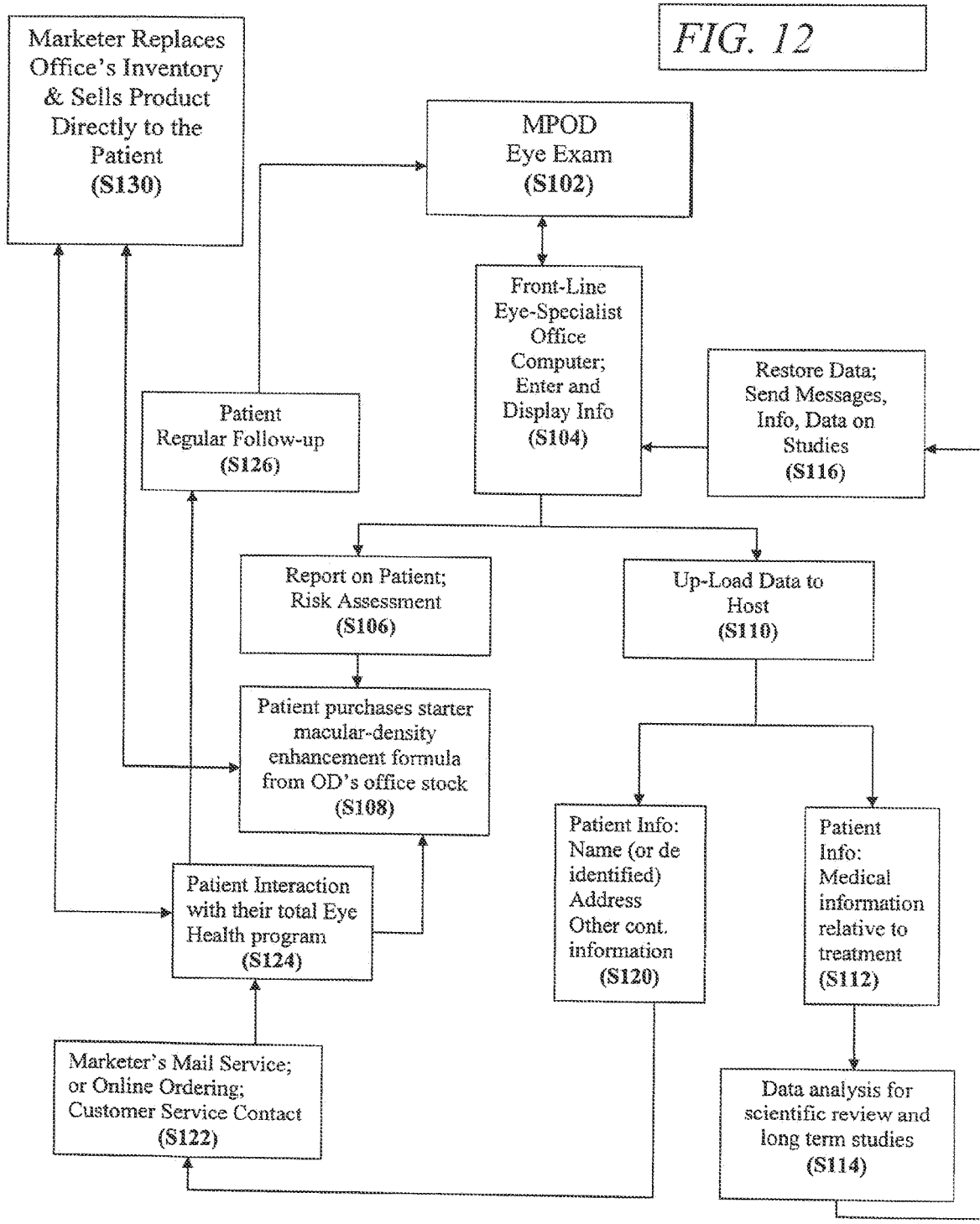
FIG. 12 illustrates one type of business method of using the system of FIG. 2 to directly provide nutritional supplements, such as macular-pigment enhancing formulas, from the marketer of such nutritional supplements.

FIG. 12 provides a schematic of one embodiment of the overall business method 100 according to the present invention. The method 100 includes the initial eye exam on the MPOD device 22 (S102) and the entry and gathering of patient information at the computer 20 (S104). The patient is then provided with some type of report and/or a risk assessment based on the results of the MPOD test and information that was gathered (S106).

Next, the patient purchases a supply of a certain nutritional supplement for the eye based on the patient's information and test results. Preferably, the sale occurs directly at the offices of the front line eye specialist (S108). The information concerning the nutritional supplement that was purchased by the patient is also recorded in the computer 20.

The relevant data related to the patient is also transferred to the host 12 (S110). The relevant data from the patient is stored within the storage device 14 associated with the host 12 (S112) and can be analyzed for scientific purposes and long-term studies (S114). The data for that patient and information related to be data analysis and long-term studies can then be transferred back to the front-line office computer 20, as needed. (S116). One example of the type of information that can be provided to the patient and/or front line eye specialist is the information illustrated in and described with respect to FIGS. 10-11.

Additionally, information related to the patient (e.g. contact information, date of previous MPOD high exam, nutritional supplement that was purchased, and possibly and MPOD results) is provided to the marketer of the recommended nutritional supplement. (S122). The transfer of this information allows the marketer to be interactive with the patient by providing them information concerning (i) the need for a possible follow-up exam, (ii) purchasing additional quantities of a certain nutritional supplement, and/or (iii) results from the long-term studies that may be helpful to the patient. Based on this patient interaction (S124), the patient may return to the same office or a different office to have a follow-up eye exam (S126). The patient may also request the office to provide another supply of additional nutritional supplements (S108). Or alternatively, and preferably, the patient may order the nutritional supplement directly from the marketer of that specific nutritional supplement. (S130). It should also be noted that the marketer may be provided with information from the office computer 20 about additional purchases from a patient (or patients) and send a communication to the office (i.e. the module 18) about the need to replenish inventory of a certain nutritional supplement. Hence, that is the purpose of the additional double-arrow connecting boxes S120 and S108.

Further, if the marketer of the nutritional supplement knows the amount that was purchased, the marketer can provide well-timed communications to the patient. The communications to patients can include discounts on the next purchase or partially reimbursing the patient for the next MPOD test if additional nutritional supplements are purchased.

Similarly, it is presumed that most patients will readily agree to participate in the data-gathering project disclosed herein, out of a desire and motivation to help reduce blindness. However, if deemed necessary and appropriate, such customers might also be provided with some type of product discount or other incentive for an eye supplement, in exchange for agreeing to allow their data to be compiled in a larger data-gathering effort at host 12.

If desired, other additional and optional steps to expand the usage of the system 10 can be added to the business method. For example, the MPOD devices 22 for measuring macular pigment can be enhanced to provide them with instructional guides and aids (such as small speakers that will play prerecorded voice instructions, a video-type presentation that can be provided separately or that can be played on the same screen that will be used for other visual displays inside the measuring device, etc.) that will enable reasonably accurate and useful macular pigment measurements to be made in locations such as drugstores, physician's waiting rooms, tables or booths that can be set up in shopping malls or other high-traffic areas, etc. In general, these types of installations will not be as well-suited for gathering statistically reliable data as installations that are supervised and run by trained personnel in a location such as an optometrist's office. However, these types of installations (i.e. less supervised modules 18) can be very useful in increasing awareness among the public of the importance of good nutrition (and, if needed, good nutritional supplements) for eye and vision health.

Thus, there has been shown and described a new and useful multi-part computerized system that will enable provide major advances in preventing and treating macular degeneration and possibly other eye diseases, and a business method that will help front-line eye specialists, such as optometrists and ophthalmologists, better serve their customers and patients, while also helping and benefiting the public interest. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

Linking Others To The System 10. The host 12 can be further linked to other computers associated with individuals who may be interested in the data being collected. For example, the host 12 could be linked to the executive directors and/or the scientific or research directors of several not-for-profit organizations that work with eye and vision research, such as the Foundation for Fighting Blindness, the Macular Degeneration Foundation, the Macular Degeneration Partnership, American Optometric Association, American Academy of Ophthalmology, and the American Academy of Optometry, etc. Or the host 12 could be linked to researchers at medical schools or eye care institutes who have worked in the past with this type of research, including: (i) researchers who worked with the National Eye Advisory Council, as listed in *Vision Research—A National Plan: 1999-2003* (NIH Publ. 99-4120, 1999) and any subsequent updates of that work; (ii) researchers who worked with the steering committees that guided the AREDS-1 study, as listed in *Arch. Ophthalmol.* 119: 1437-1438, 2001); (iii) researchers who worked with the Eye Disease Case Control Study Group, as listed in *Arch. Ophthalmol.* 11: 104-109 (1993) and *Arch. Ophthalmol.* 10: 1701-1708 (1992); and, (iv) researchers who worked with the Carotenoids in Age-Related Eye Disease Study (CAREDS), as listed in Snodderly et al 2004; or (v) researchers and officials at the National Eye Institute, who are currently planning and arranging public funding for the AREDS-2 trial.

Checking For Other Eye Disorders At The Modules 18. In at least some cases, an MPOD device 22 or the computer 20 can be designed and adapted to carry out additional types of measurements as well. This is especially true when considering devices that use flicker photometry to measure MPOD. Such devices provide both (i) an aperture with a lens, which the user must look into, and (ii) a controllable light-presenting display, inside the MPOD device 22. The types of controllable light-presenting devices and displays that can be provided, in a device that is designed and suited for flicker photometry, can also provide other displays that can enable measurements of, for example, dark adaptation, glare recovery, shape discrimination, etc. Similarly, the retinal damage that has been inflicted by glaucoma or various other eye diseases can be measured, and even mapped, by having a patient respond to faint pinpoint-type light emissions that appear at various locations around the visual field, as the patient focuses on a specific point somewhere on a display screen. These measurements are sometimes referred to as "Humphrey perimetry" measurements, made from instruments produced by Humphrey Instruments, Incorporated of California. Light-emitting diodes or other electronic components that can enable those types of measurements can be provided in flicker photometer devices, and possibly in various other type of devices that can also measure MPOD levels.

It should also be noted that numerous completely different types of devices and methods have been developed for measuring various eye conditions, including some conditions that can be affected by macular pigment levels. As examples, optometrists and ophthalmologists use various known devices and tests to measure factors such as: (1) how quickly a patient's eyes and vision can adapt to abrupt and major changes in light/dark conditions; (2) how well a patient's eyes and vision can handle glare conditions; (3) how accurately a patient can detect tiny or subtle differences in shapes, such as by comparing circles that are nearly but not exactly circular; (4) how sensitively various parts of the retina can detect faint flickering lights that appear in different locations within the visual field; and, (5) intra-ocular fluid pressures, which become crucially important in patients with glaucoma. Those are just a few examples of the types of diagnostic tests that can be used to evaluate eye health, based on factors other than the types of near-sightedness, far-sightedness, or astigmatic vision problems that are normally addressed by corrective lenses or laser surgery. The present invention contemplates the use of other devices as peripherals to the computer 20 with the system 10 to gather other data as well. As one example, the module 18 may include the computer 20, the MPOD device 22, and a secondary device for measuring the fluid pressure in the eye. As another example, the module 18 may include the computer 20, the MPOD device 22, and the computer 20 may also provide for an automated Amsler grid test.

While the illustrated embodiments have been described with regard to the MPOD testing, the present invention contemplates an eye health measurement and storage system. The system comprises a plurality of macular-function measurement machines and a central host. The plurality of macular-function measurement machines measure macular function in humans (e.g., dark adaptation, shape discrimination, etc.). Each of the macular-function measuring machines includes a device for receiving macular function data from a patient, at least one data transfer port, and at least one processor that enables the transfer of the macular function data from the transfer port. The central host is coupled to the transfer ports on each of the plurality of computers. The central host includes a processor adapted to (i) store the patient data in a storage device and (ii) transmit macular-function study data to test locations associated with the plurality of macular-function measurement machines.

Further, while the MPOD device 22 and the computer 20 has been described as being two separate devices, the present invention contemplates a single MPOD device 22 having its own storage device, user input device, and display. The patient would enter patient information and view displayed information via the integral display on the MPOD device 22. The MPOD device 22 could still be linked to a computer within the office, but for the purpose of transmitting information to that computer and the host 12. Or, the MPOD device 22 would include a wireless networking card allowing it to be separately linked to a wireless router (e.g. a Linksys® Wireless 2.4 GHz Broadband Router) within the office. At periodic intervals, the MPOD device 22 would simply access the Internet via the wireless router and send the needed information to the host 12. This is beneficial since the MPOD device is then free standing, only needing to plugged into a power outlet in the office.

Each of these embodiments and obvious variations thereof is contemplated as falling within the spirit and scope of the claimed invention, which is set forth in the following claims.

Many of the articles and publications on the attached list have been referenced above. Each of these articles is incorporated by reference in its entirety.

1. "Fast and Objective Measurement Of Macular Pigment With Natural Pupil" (Dirk van Norren, Jan van de Kraats, Suze Valen & Tos T. J. M. Berendschot) April 2005—(1-page)
2. "Fundus Photography For Measurement Of Macular Pigment Density Distribution in Children"
   (Lo J. Bour, Lily Koo, Francois C. Delort, Patricia Apkarian, Anne B. Fulton) Investigative Ophthalmology & Visual Science, May 2002, Vol. 43, No. 5 Copyright© Association for Research in Vision and Ophthalmology—(7-pages)
3. "Comparison Of Fundus Autofluorescence and Minimum-Motion Measurements Of Macular Pigment Distribution Profiles Derived From Identical Retinal Areas" Anthony G. Robson, Glen Harding, Frederick W. Fitzke, Jack D. Moreland "Perception" Volume 34 2005—www.perceptionweb.com—(7-pages)
4. "Macular Pigment Assessment By Motion Photometry" Moreland J D.—MacKay Institute, Keele University, Staffordshire, ST5 5BG, UK. j.d.moreland@cms.keele.ac.uk
PubMed—Arch Biochem Biophys. 2004 Oct. 15; 430(2): 143-8—(1-page)
5. "Macular Pigment Optical Density Measurement: A Novel Compact Instrument" Stephen Beatty, Hui-Hiang Koh, David Carden and Ian J. Murray, Ophthal. Physical Opt. Vol. 20, No. 2, pp. 105-111, 2000
©2000 The College of Optometrists, Published by Elsevier Science Ltd. Printed in Great Britain—(7-pages)
6. "A Practical Method For Measuring Macular Pigment Optical Density" Billy R. Wooten, Billy R. Hammond, Jr., Richard I. Land and D. Max Snodderly Investigation Ophthalmology and Visual Science. 1999; 40:2481-2489.)
©1999 by The Association For Research In Vision and Ophthalmology, Inc. (14 pages)
7. "Macular Pigment Measurement By Heterochromatic Flicker Photometry In Order Subjects: The Carotenoids And Age-Related Eye Disease Study" D. Max Snodderly, Julie A. Mares, Billy R. Wooten, Lisa Oxton, Michael Gruber, and Tara Ficek, for the AREDS Macular Pigment Study Group Investigative Ophthalmology & Visual Science, February 2004, Vol. 45, No. 2 Copyright ©Association for Research in Vision and Ophthalmology.—(8-pages)
8. "Macular Pigment"
Property of the University of Westminster, Vision Research Group John Mellerio—mellerj@wmin.ac.uk—(10 pages)
9. "Heterochromatic Flicker Photometry"
Department of Physics, Florida International University, Miami 33199, USA Bone R A, Landrum J T.—bone@fiu.edu
PubMed—Arch Biochem Biophys. 2004 Oct. 15; 430(2): 137-42—(1 page)
10. "A Portable Instrument For Measuring Macular Pigment With Central Fixation" Mellerio J, Ahmadi-Lari S, van Kuijk F, Pauleikhoff D, Bird A, Marshall J. School of Biosciences, University of Westminster, London, UK.
PubMed—Curr Eye Res. 2002 July; 25(1):37-47—(1 page)
11. "Macular Pigment Density Measured By Autofluorescence Spectrometry: Comparison with Reflectometry and Heterochromatic Flicker Photometry"
Delori F C, Goger D G, Hammond B R, Snodderly D M, Burns S A. Schepens Eye Research Institute, Boston, Massachusetts 02114, USA.
PubMed—Opt Soc Am A Opt Image Sci Vis. 2001 June; 18(6):1212-30.—(1 page)
12. "Autofluorescence Method To Measure Macular Pigment Optical Densities Fluorometry And Autofluorescence Imaging"
Francois C. Delori
Schepens Eye Research Institute and Harvard Medical School, Boston, M.A. USA ©2004 Published by Elsevier Inc.—(7 pages)
13. "Resonance Raman Measurement of Macular Carotenoids In The Living Human Eye"
Paul S. Bernstein, Da-You Zhao, Mohsen Sharifzadeh, Igor V. Ermakov, Werner Gellermann
Department of Ophthalmology and Visual Sciences, Moran Eye Center, University of Utah School of Medicine, Salt Lake City, UT, USA, Department of Physics, University of Utah, Salt Lake City, UT
©2004 Elsevier Inc.—(7 pages)
14. "Influence of Lutein Supplementation On Macular Pigment, Assessed with Two Objective Techniques"
Tos T. J. M. Berendschot[1], R. Alexandra Goldbohm[2], Wilhelmina A. A. Klöpping[2], Jan van de Kraats[1], Jeannette van Norel[1], and Dirk van Norren[1]
©2000 by The Association for Research in Vision and Ophthalmology, Inc.—(1 page)
15. "Influence Of Lutein Supplementation On Macular Pigment, Assessed With Two Objective Techniques"
Berendschot T T, Goldbohm R A, Klopping W A, van de Kraats J, van Norel J, van Norren D.
University Medial Centre Utrecht, Department of Ophthalmology, The Netherlands PubMed—Invest Ophthal. Vis. Sci. 2000 October; 41(11):3322-6.—(1 page)
16. "Objective Determination Of The Macular Pigment Optical Density Using Fundus Reflectance Spectroscopy"
Tos T. J. M. Berendschot* and Dirk van Norren
Department of Ophthalmology, University Medical Center Utrecht, The Netherlands ©2004 Elsevier, Inc.—(7-pages)
17. "Current Concepts In The Pathogenesis Of Age-Related Macular Degeneration" Marco A. Zarbin, MD, PhD.
Arch Ophthalmol./Vol. 122. April 2004—www.archophthalmol.com
©2004 American Medical Association.—(17 pages)
18. "Assessment Of The Validity Of In Vivo Methods Of Measuring Human Macular Pigment Optical Density"
Hammond B R Jr., Wooten B R, Smollon B.
Vision Science Laboratory, University Of Georgia, Athens, Georgia 30602-3013, USA
PubMed—Optom Vis. Sci. 2005 May; 82(5):387-404—(1 page)
19. "In Vivo Assessment Of Retinal Carotenoids: Macular Pigment Detection Techniques and Their Impact On Monitoring Pigment Status"
Joanne Curran Celentano, Joanne D. Burke and Billy R Hammond, Jr.
Department of Animal and Nutritional Sciences, University of New Hampshire, Durham, NH and Department of Psychology and Behavior Sciences, University of Georgia, Athens, GA ©2002 American Society For Nutritional Sciences—(5 pages)
20. "Macular Degeneration—The Latest Scientific Discoveries and Treatments For Preserving Your Sight"
Robert D'Amato, M.D., Ph.D., and John Snyder
Copyright ©2000 by Robert d'Amato and Joan Snyder—(2 pages)
21. "Age-Related Macular Degeneration"
Jeffrey W. Gerger, Stuart L. Fine and Maureen G. Maguire, Mosby, 1999. July 2002/576 pp, illus./ISBN: 08247-0682-X—(3-pages.)

The invention claimed is:

1. A method of improving vision in human patients, comprising:
obtaining eye-health information from a first patient, the eye-health information including data obtained by an instrument that measures a characteristic of the eyes of the first patient and at least three of the group consisting of eye color, age, gender, smoking status, medical status, previously diagnosed eye disease, intake of nutritional supplements, genetic information, and diet;
transmitting the eye-health information associated with the first patient to a central host;
receiving, from the central host, an eye-health assessment of the first patient based on the eye-health information from the first patient, the eye-health assessment being determined by a statistical analysis of other eye-health information from a plurality of patients that is stored in a storage device accessible by the central host; and in response to the eye-health assessment, providing the first patient with a recommendation for improving visual performance of the first patient.

2. The method of claim 1, wherein the instrument is a macular-pigment measurement machine for receiving macular-pigment data from the patient.

3. The method of claim 1, wherein the instrument is a fundas camera.

4. The method of claim 1, wherein the previously diagnosed eye disease is diabetic retinopathy.

5. The method of claim 1, wherein the medical status includes information regarding diabetes.

6. The method of claim 1, wherein the recommendation includes a recommendation for a first carotenoid mixture to increase a macular pigment of the first patient.

7. The method of claim 1, wherein the obtaining the eye-health information from the first patient includes receiving information from the first patient at a computer.

8. The method of claim 7, wherein the obtaining the eye-health information from the first patient includes receiving information from a peripheral device that is coupled to the computer.

9. The method of claim 1, wherein the instrument is one of a group consisting of a scanning laser opthalmoscope, a reflectometry device, a flicker photometry device, autofluorescence device, a Raman-scattering device, an anomalscope, and a modified fundas camera.

10. The method of claim 1, wherein the recommendation includes a suggested dosage of a nutritional formulation.

11. The method of claim 10, wherein the nutritional formulation includes zeaxanthin.

12. The system of claim 1, wherein the central host includes a website that is configured to receive the transmitted eye-health information for the plurality of patients.

13. A method of improving vision in human patients, comprising:
obtaining eye-health information from a first patient, the eye-health information including data obtained by an instrument that measures a characteristic of the eyes of a first patient and at least three of the group consisting of eye color, age, gender, smoking status, medical status, previously diagnosed eye disease, intake of nutritional supplements, genetic information, and diet;
transmitting the eye-health information associated with the first patient to a central host; and
receiving an eye-health assessment for the first patient, the eye-health assessment for the first patient being based on the eye-health information associated with the first patient and a statistical analysis of other eye-health information from a plurality of patients that is stored in a storage device accessible by the central host.

14. The method of claim 13, wherein the instrument is a macular-pigment measurement machine for receiving macular-pigment data from the first patient.

15. The method of claim 14, wherein the eye-health assessment includes a recommendation for a nutritional formulation with carotenoids for improving visual performance of the first patient.

16. The method of claim 13, wherein the instrument is one of a group consisting of a scanning laser opthalmoscope, a reflectometry device, a flicker photometry device, autofluorescence device, a Raman-scattering device, an anomalscope, and a modified fundas camera.

17. The system of claim 13, wherein the central host includes a website that is configured to receive the eye-health information for the plurality of patients.

18. The method of claim 17, wherein the instrument is a macular-pigment measurement machine for receiving macular-pigment data from the first patient.

19. The method of claim 17, wherein the recommendation includes a suggested nutritional formulation that includes zeaxanthin.

20. The method of claim 13, wherein the eye-health assessment includes a recommendation for improving visual performance of the first patient.

21. A method of improving vision in human patients, comprising:
receiving, at a central host, eye-health information from a first patient, the eye-health information including (i) data obtained by an instrument that measures a characteristic of the eyes of a first patient and (ii) at least three of the group consisting of eye color, age, gender, smoking status, medical status, previously diagnosed eye disease, intake of nutritional supplements, genetic information, and diet;
by use of a statistical analysis of other eye-health information from a plurality of patients that is stored in a storage device accessible by the central host, determining an eye-health assessment for the first patient based on the eye-health information from the first patient; and
transmitting, from the central host, the eye-health assessment to the first patient.

22. The method of claim 21, wherein the instrument is a macular-pigment measurement machine for receiving macular-pigment data from the patient.

23. The method of claim 21, wherein the instrument is a fundas camera.

24. The method of claim 21, wherein the previously diagnosed eye disease is diabetic retinopathy.

25. The method of claim 21, wherein the medical status includes information regarding diabetes.

26. The system of claim 21, wherein the central host includes a website that is configured to receive the other eye-health information for the plurality of patients.

* * * * *